(12) United States Patent
Yanuma

(10) Patent No.: US 8,562,601 B2
(45) Date of Patent: Oct. 22, 2013

(54) MEDICAL INSTRUMENT FOR ENDOSCOPE AND TREATMENT METHOD

(75) Inventor: Yutaka Yanuma, Tokyo (JP)

(73) Assignee: Olympus Medical Systems Corp., Tokyo (JP)

(*) Notice: Subject to any disclaimer, the term of this patent is extended or adjusted under 35 U.S.C. 154(b) by 236 days.

(21) Appl. No.: 12/136,345

(22) Filed: Jun. 10, 2008

(65) Prior Publication Data

US 2010/0298634 A1 Nov. 25, 2010

Related U.S. Application Data

(60) Provisional application No. 60/934,151, filed on Jun. 11, 2007.

(51) Int. Cl.
*A61B 18/18* (2006.01)

(52) U.S. Cl.
USPC ............... 606/39; 606/46; 606/127; 604/916

(58) Field of Classification Search
USPC .................... 606/32, 34, 39, 41, 45, 46, 127; 604/916
See application file for complete search history.

(56) References Cited

U.S. PATENT DOCUMENTS

| | | | |
|---|---|---|---|
| 4,886,496 A * | 12/1989 | Conoscenti et al. | 604/103.11 |
| 5,628,746 A * | 5/1997 | Clayman | 606/45 |
| 5,683,362 A * | 11/1997 | Rowland et al. | 604/96.01 |
| 5,766,151 A | 6/1998 | Valley et al. | |
| 2002/0068879 A1* | 6/2002 | Lubock et al. | 600/567 |
| 2005/0209674 A1 | 9/2005 | Kutscher et al. | |
| 2006/0247494 A1 | 11/2006 | Nakagawa et al. | |
| 2008/0125803 A1 | 5/2008 | Sadamasa et al. | |

FOREIGN PATENT DOCUMENTS

| | | |
|---|---|---|
| EP | 0974375 A1 | 1/2000 |
| EP | 1 886 634 A1 | 2/2008 |
| JP | 6-63057 A | 3/1994 |
| JP | 10-146389 A | 6/1998 |
| JP | 10-511283 A | 11/1998 |
| JP | 2004-275785 | 10/2004 |
| JP | 2004-532668 A | 10/2004 |
| WO | WO 96/19256 A2 | 6/1996 |
| WO | WO 02/056784 A2 | 7/2002 |
| WO | WO 2006/129726 A1 | 12/2006 |

OTHER PUBLICATIONS

Extended European Search Report dated Mar. 2, 2010.
Extended European Search Report dated Jul. 7, 2011.
Notice of Reasons for Rejection dated Dec. 11, 2012 from corresponding Japanese Patent Application No. 2008-147994 together with an English language translation.

* cited by examiner

*Primary Examiner* — Nicholas Lucchesi
*Assistant Examiner* — Leah Stohr
(74) *Attorney, Agent, or Firm* — Scully, Scott, Murphy & Presser, P.C.

(57) ABSTRACT

A medical instrument for an endoscope according to the invention is the medical instrument to be used in the endoscope by being inserted therein, and the medical instrument includes: a flexible elongated sheath having a first lumen and a second lumen; a conductive wire which is inserted into the first lumen and of which a portion of a distal side is exposed to the outside of the sheath as an instrument unit; and a balloon which is attached to the sheath and is expandable with the supply of fluid from the second lumen. The balloon is configured such that an axial dimension thereof is larger than a radial dimension upon expansion and a distal end of the balloon upon expansion is located closer to a proximal side than the treatment unit exposed from the sheath.

4 Claims, 37 Drawing Sheets

MEDICAL INSTRUMENT FOR ENDOSCOPE AND TREATMENT METHOD

BACKGROUND OF THE INVENTION

1. Field of the Invention

The present invention relates to a medical instrument for an endoscope which is used by passing through the endoscope and a treatment method.

2. Description of Related Art

A procedure for removing a calculus may be performed as an endoscopic procedure. In this case, since a papillary area, which is an exit of a bile duct, is narrow, no calculus can be discharged as it is. Accordingly, the calculus is taken out after a tear sphincter is incised by a papillotome passing through an endoscope and the exit of the bile duct is then expanded.

For example, a conventional papillotome is disclosed in Japanese Patent Application, Publication No. 2004-275785. The papillotome passes a treatment channel of an endoscope and projects from a distal end of the endoscope. A distal portion of the papillotome is inserted into a bile duct through a papilla in accordance with torsion of an inserting portion of the endoscope, adjustment of curvedness, upward and downward movements of an erecting device, and advance and retreat operations of the papillotome itself. If necessary, a guide wire is inserted into a lumen of the papillotome. When a knife is stretched by operating a handy operating portion of the papillotome and radio-frequency current is applied thereto, a teat sphincter is incised and an exit of the bile duct is enlarged.

In the state in which the guide wire is left in the bile duct, only the papillotome is removed from the bile duct and the channel of the endoscope. Next, a basket or a balloon for collecting a calculus is inserted through the guide wire. The basket or the balloon is directed up to an upstream of the calculus along the guide wire. In the case of basket, the basket is opened by a hand-side operation. In the case of balloon, the balloon is supplied with air by a syringe from a hand side and thereby swollen. In this state, when the basket or the balloon is taken out toward the exit of the bile duct, the calculus is captured by the basket or the balloon and discharged together to the outside of the bile duct.

In this procedure, the papilla is incised by the papillotome such that an opening of the exit of the bile duct is enlarged. However, when an incision length is too short or the calculus is too large, the calculus is stuck in the exit of the bile duct and cannot be discharged. In this case, the calculus is collected by surgery, or endoscopically-collected by being destroyed with ESWL (extracorporeal shock wave lithotripsy) and thereby being reduced in size. Otherwise, the calculus is collected using the above-described basket or balloon by being endoscopically-destroyed and thereby being reduced in size.

In addition, when the papilla is largely incised by the papillotome, the calculus is easily extracted. However, when a blood vessel near the papilla is cut, bleeding is caused. In general, incision up to an upper edge of a projection on an entrance side of the papilla is referred to as large incision, two thirds of the incision is referred to as medium incision, and one third of the incision is referred to as small incision. Since a possibility of existence of a blood vessel more increases as nearer to the upper edge of the projection, a possibility of bleeding is higher in the medium incision than in the small incision and is higher in the large incision than in the medium incision. In general, an opening of about 5 mm is formed by the medium incision. Since the opening has a stretching property to some extent, a calculus having a size up to about 10 mm can be discharged. Today, the medium incision is mainly performed from the viewpoint of a risk of bleeding. The calculus having a size up to about 10 mm is collected without destruction, however, a calculus having a size more than 10 mm is collected using a complicated procedure, as described above.

As a method having a small risk of bleeding, there is a method of expanding the papilla by a dilation balloon having a withstand pressure instead of the incision with the papillotome.

SUMMARY OF THE INVENTION

A medical instrument for an endoscope according to a first aspect of the invention includes: a flexible elongated sheath which is inserted into the endoscope; a balloon which is attached to a distal end of the sheath to introduce a body and is expandable with a supply of fluid; and a lumen which supplies the fluid to the balloon. The balloon is configured such that an axial dimension thereof is larger than a radial dimension thereof upon expansion.

A medical instrument for an endoscope according to a second aspect of the invention includes: a flexible elongated sheath which is inserted into the endoscope; a first balloon which is attached to an outer circumference of a distal end of the sheath to introduce a body and is expandable with a supply of fluid; a second balloon which is attached to the outer circumference of the distal end of the sheath and is expandable with the supply of fluid; and two lumens for supplying the fluid to first and second balloons respectively. The second balloon is disposed on outer circumference of the sheath at a position closer to a distal side than the first balloon, and an axial length of the second balloon is shorter than that of the first balloon.

A treatment method according to a third aspect of the invention includes: introducing a flexible elongated sheath into a body through the endoscope; applying current to an exposed conductive wire at a distal end of the sheath to incise tissue and enlarge a diameter of a channel; inserting the sheath into the channel to advance a balloon, which is provided closer to a proximal side than the conductive wire on an outer circumference of the sheath, into the channel; and swelling the balloon such that an axial length thereof is longer than a radial length to enlarge the channel incised by the conductive wire.

DETAILED DESCRIPTION OF THE INVENTION

Figure 1:
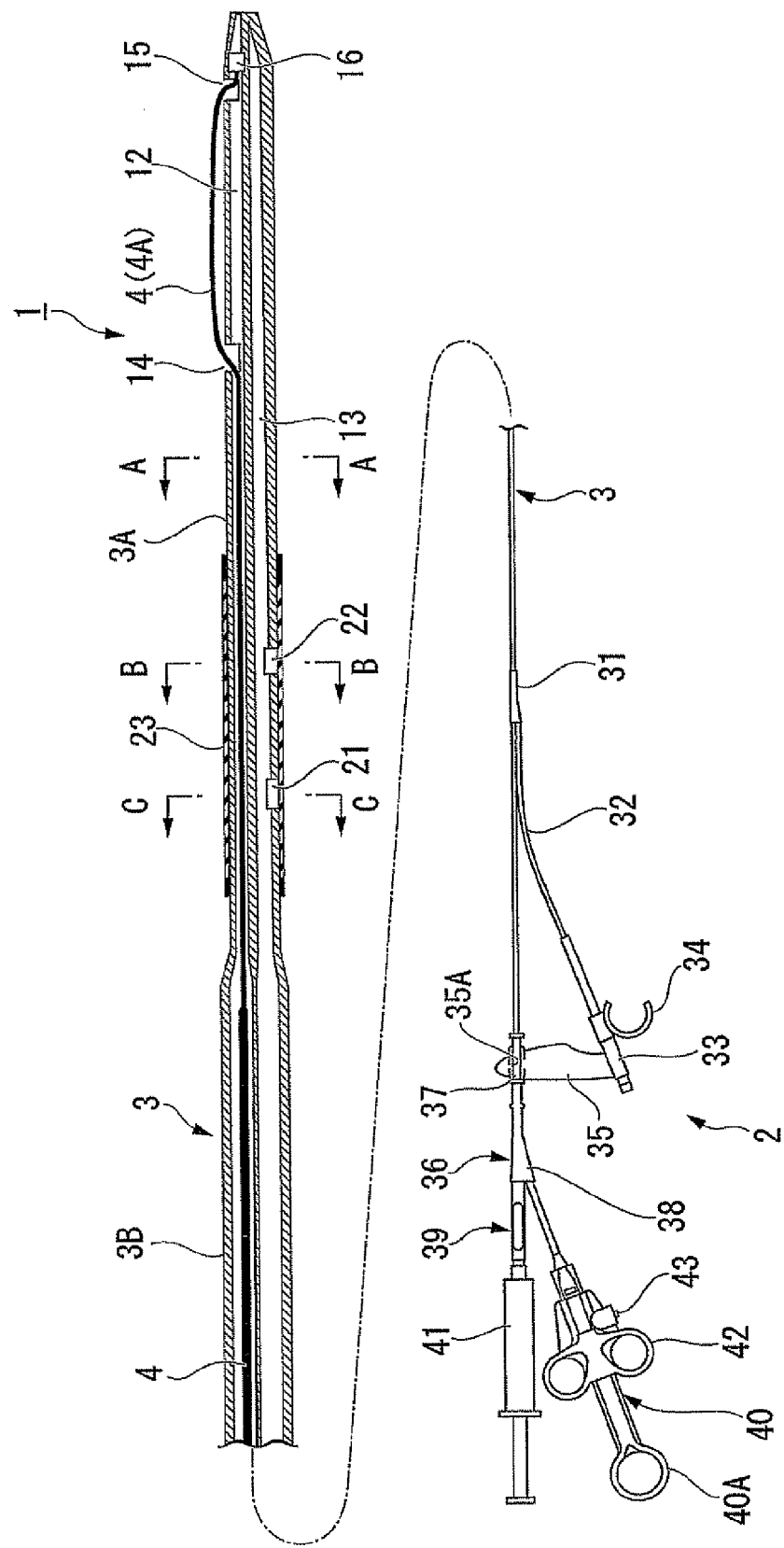
FIG. 1 is a diagram showing the configuration of a papillotome which is an example of a medical instrument for an endoscope.
Figure 2:
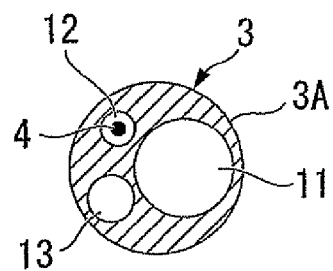
FIG. 2 is a cross-sectional view taken along the line A-A of FIG. 1.
Figure 3:
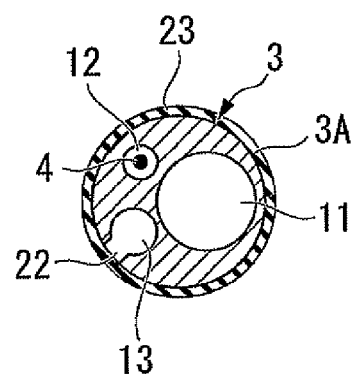
FIG. 3 is a cross-sectional view taken along the line B-B of FIG. 1.
Figure 4:
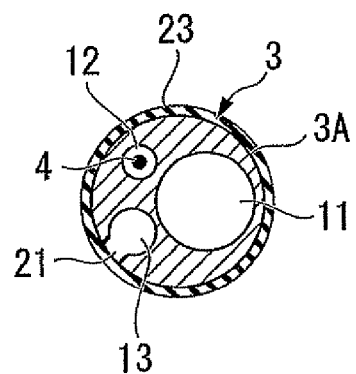
FIG. 4 is a cross-sectional view taken along the line B-B of FIG. 1.

Embodiments will now be described. It is to be noted that, in the embodiments, a common part is denoted with the same reference numeral, and redundant description is omitted.

First Embodiment

FIG. 1 shows the configuration of a papillotome which is an example of a medical instrument for an endoscope. The papillotome 1 has an operating portion 2 to be operated by an operator and a flexible elongated sheath 3 which extends from the operating portion 2. A conductive wire 4 as a treatment unit is drawn out of a side portion on a distal side of the sheath 3.

In the sheath 3, a distal portion 3A from which the conductive wire 4 is drawn out is reduced in diameter than the other portion 3B. For example, a diameter of the distal portion 3A is about 1.8 mm to 1.9 mm, and a diameter of the other portion 3B is about 2.4 mm to 2.6 mm. Insertion capability into a papilla becomes better by reducing a diameter of a distal end.

As shown in FIGS. 1, 2, 3 and 4, the sheath 3 has three lumens 11, 12 and 13 which are formed substantially parallel to a longitudinal direction. The first lumen 11 has the largest diameter and is open at a distal end thereof. The lumen 11 is used to insert a guide wire and inject a contrast agent therethrough. The second lumen 12 has the smallest diameter and is sealed at a distal end thereof. On a distal side of the second lumen 12, two holes 14 and 15, which are open to a side portion of the sheath 3, are formed at a front portion and a rear portion in the longitudinal direction. The conductive wire 4 passes through the second lumen 12. A distal side of the conductive wire 4 is reduced in diameter to be fitted in the distal portion 3A of the sheath 3 which is reduced in diameter. In addition, the conductive wire 4 is drawn out to the outside of the sheath 3 from the hole 14 formed on the side portion of the distal portion 3A of the sheath 3, and directed again into the second lumen 12 from the hole 15 provided on the distal side. The portion which is exposed by being drawn out to an outer circumference of the sheath 3 becomes an incision knife portion 4A. A distal end of the conductive wire 4 is fixed to the sheath 3 through a tip 16.

The third lumen 13 is sealed on a distal side thereof. On the distal side of the third lumen, two holes 21 and 22, which are open to the side portion of the sheath 3, are formed at a front portion and a rear portion in the longitudinal direction. These holes 21 and 22 are disposed closer to a proximal side than the holes 14 and 15 of the second lumen 12. A balloon 23 is attached to the distal portion 3A of the sheath 3 as a dilator so as to cover the holes 21 and 22.

The balloon 23 is disposed apart from the incision knife portion 4A (that is, hole 14) by a distance of about 1 to 2 cm. This allows the balloon 23 not to be caught by an erecting base of the endoscope when incision of the papilla is performed. A distal portion and a proximal portion of the balloon 23 are fixed to the sheath 3 in an annular shape by heat-welding or using an adhesive or a piece of string. The balloon 23 in an initial state is in close contact with the outer circumference of the sheath 3, and an outer diameter of the balloon is equal to or less than an outer diameter of the portion 3B on the proximal side of the sheath 3. The holes 21 and 22 are disposed at positions defined by dividing a length parallel to a longitudinal direction of the balloon 23 in close contact into substantially three. Otherwise, instead of the two holes 21 and 22, there may be one long hole including the positions of the two holes 21 and 22.

Figure 5:
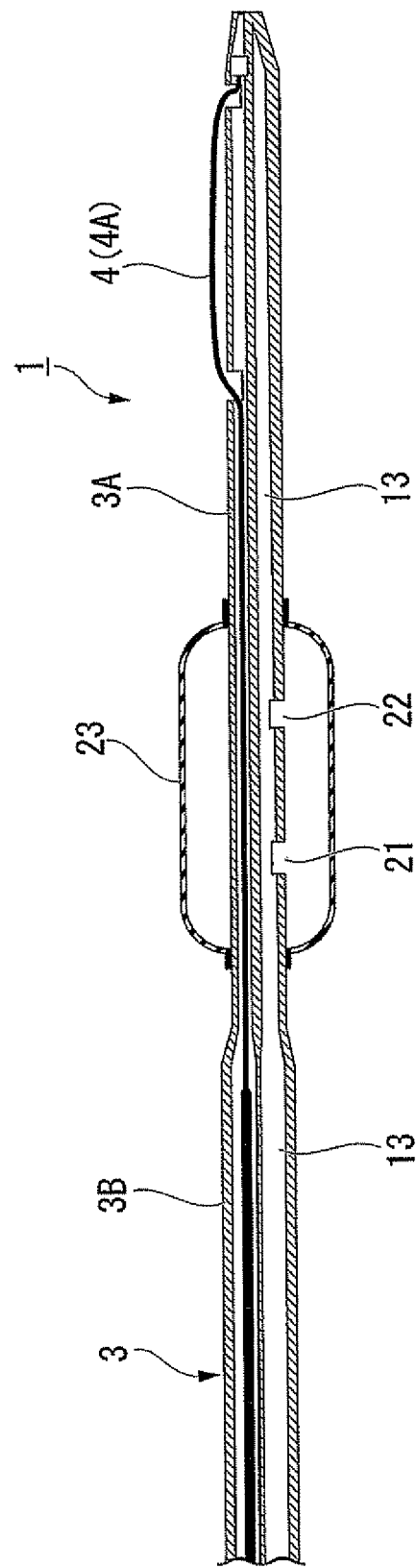
FIG. 5 is a cross-sectional view showing a state in which a balloon is swollen.

The balloon 23 is made of an elastomeric material having a high stretching property, such as latex or silicon. The most preferable material is latex which has the highest stretching property. FIG. 5 shows the appearance when the balloon 23 is swollen. The largest expansive diameter of the balloon 23 is about 16 to 20 mm. The length thereof in the longitudinal direction is 1.5 to 2 times the largest expansive diameter (specifically, 30 to 40 mm). In the case of using latex, the diameter of the balloon before shrinkage is about $\phi$2.0 mm to 2.5 mm to obtain an expansive diameter of 20 mm since the maximum elongation of the latex is about 800% to 1000%.

The operating portion 2 shown in FIG. 1 has a first branching portion 31 attached to the sheath 3. The first branching portion 31 is used to allow the first lumen 11 in the sheath 3 to communicate with a tube 32. The tube 32 is provided with a flexible inserting portion 33 through which the guide wire can be inserted from an end portion. A ring 34 is formed on a side portion of the inserting portion 33. The ring 34 is open at a distal side thereof and has a substantially C-like shape. When fitting the ring 34 into the endoscope, the operating portion 2 can be fixed to the endoscope. In addition, a connecting portion 35 integrally extends from the side portion of the inserting portion 33 at a side substantially opposite to an extending direction of the ring 34. A concave portion 35A is formed at a distal end of the connecting portion 35.

Further, the operating portion 2 has an operating portion main body 36 fixed to a proximal portion of the sheath 3 which is an end portion extending beyond the first branching portion 31. The operating portion main body 36 is provided with an engaging portion 37 at a distal end thereof. The engaging portion 37 can be attached to and removed from the concave portion 35A of the connecting portion 35. The operating portion main body 36 is branched into a first operation unit 39 and a second operation unit 40 through a second branching portion 38 from the engaging portion 37. The first operation unit 39 is disposed on a same axis of the sheath 3, communicates with the third lumen 13, and has a syringe 41 removably attached to an end portion thereof. The second operation unit 40 is tilted with respect to the first operation unit 39, and has a slider 42 attached thereto such that the slider can advance and retreat. A terminal 43 which can be connected to an exterior radio-frequency power source is attached to the slider 42, and electrically connected to the conductive wire 4 fixed to the slider 42.

Next, a procedure using the papillotome 1 will be described.

Figure 6:
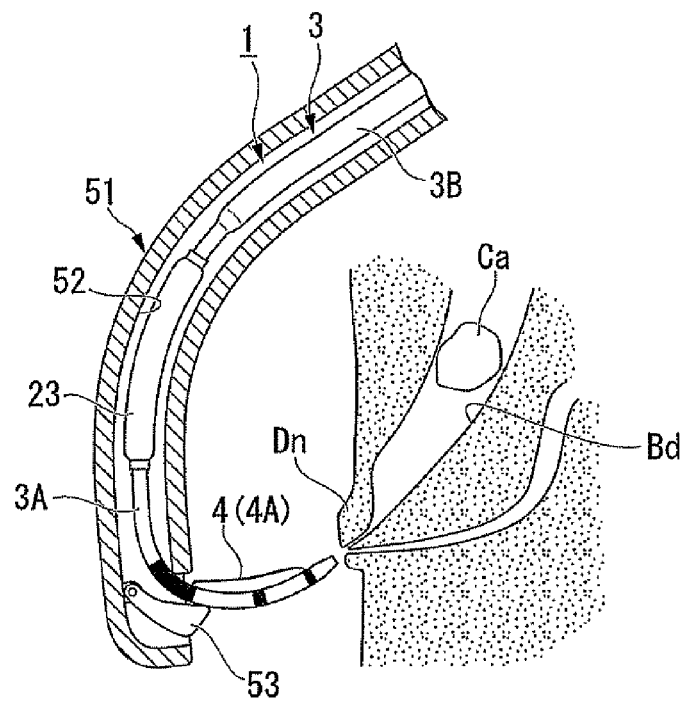
FIG. 6 is a diagram showing a state in which the papillotome passing through the endoscope is guided to the vicinity of a papilla.

First, the endoscope is inserted from a mouth, which is a natural opening of a patient, and introduced to a duodenum. An image about internal parts of a body is taken by an observation device attached to the endoscope acquires, and a distal portion of the endoscope is guided to the vicinity of papilla. As shown in FIG. 6, the papillotome 1 is inserted into a work channel 52 of the endoscope 51 to project the distal portion 3A from the endoscope 51. An erecting base 53 provided at a distal end of the endoscope 51 is operated by hand to allow a distal portion of the papillotome 1 to be directed to the papilla Dn. In this step, the balloon 23 is not expanded. In addition, the procedure is easily performed when a side vision type endoscope which has a lateral observation view is used as the endoscope 51.

Figure 7:
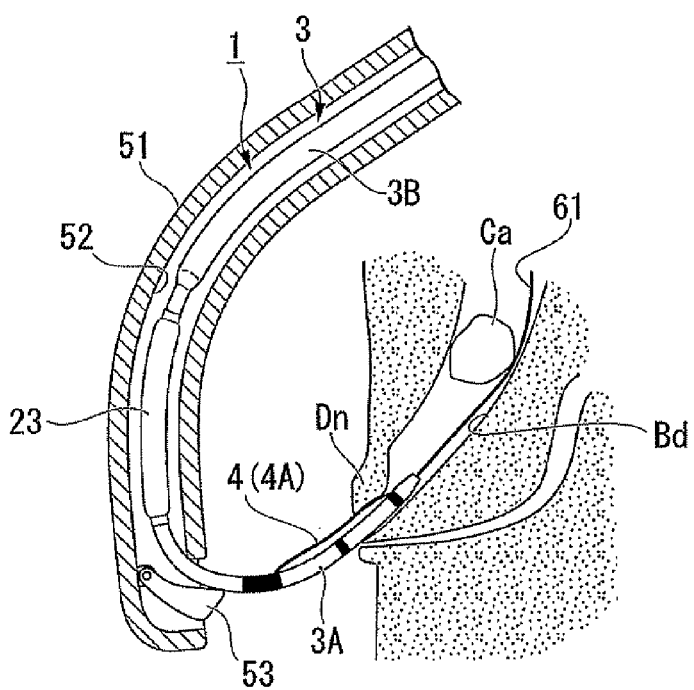
FIG. 7 is a diagram showing a state in which a distal end of the papillotome is inserted into the papilla.
Figure 8:
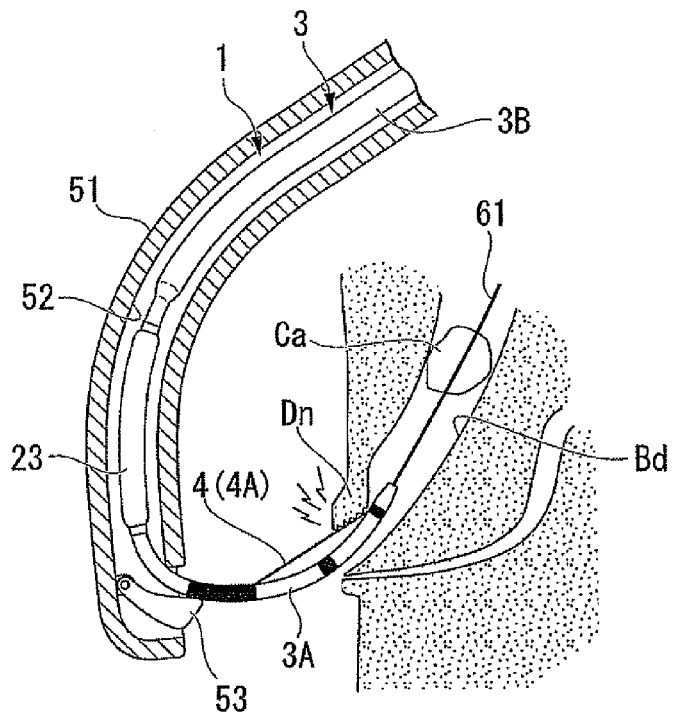
FIG. 8 is a diagram showing a state in which the papilla is incised by an incision knife portion of the papillotome.
Figure 9:
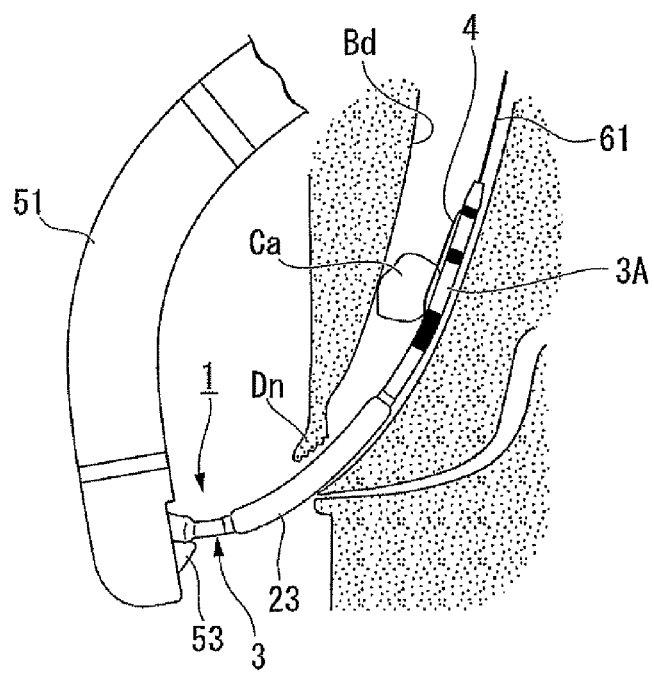
FIG. 9 is a diagram showing a state in which the papillotome after incision is advanced into a bile duct.

When the papilla Dn is incised, as shown in FIG. 7, the distal end of the sheath 3 is inserted into the papilla Dn. The guide wire is inserted from the inserting portion 33 of the operating unit 2 and introduced into a bile duct. The guide wire may not be necessarily used. However, when allowing passage of the guide wire, it is more reliable to incise the papilla, or it is convenient to exchange with another medical instrument. Further, the radio-frequency power source is connected to the terminal 43 of the slider 42 of the second operation unit 40. Fingers are placed on a ring 40A at a proximal end of the second operation unit 40 and the slider 42 to retreat the slider 42 to thereby pull the conductive wire 4. Since the distal end of the conductive wire 4 is fixed to the distal portion 3A of the sheath 3, the distal portion 3A of the sheath 3 is curved, and the incision knife portion 4A in which the conductive wire 4 is exposed to the outside of the sheath 3 is stretched in an arc shape. While radio-frequency current is transmitted from the radio-frequency power source to the conductive wire 4 through the terminal 43, the erecting base 53 is operated to allow the sheath 3 to swing. As shown in FIG. 8, the papilla Dn which is in contact with the incision knife portion 4A is incised. An incision amount of the papilla Dn is set to a half-incision or small-incision degree having little possibility of bleeding. Moreover, when the slider 42 is pushed to advance, the incision knife portion 4A of the conductive wire 4 can be bulged toward the outside of a radial direction. The application of the radio-frequency current is stopped to retreat the slider 42, and after that, the sheath 3 is further advanced into a bile duct Bd along a guide wire 61. As shown in FIG. 9, the papillotome 1 is advanced such that the balloon 23 reaches from the papilla Dn to the inside of the bile duct Bd. Preferably, while an endoscope image is observed, an insertion amount is adjusted such that a substantially central portion in an axial direction of the balloon 23 reaches to the papilla Dn. Then, the papilla Dn and a circumference thereof can be securely pressed and enlarged when the balloon 23 is swollen.

Figure 10:
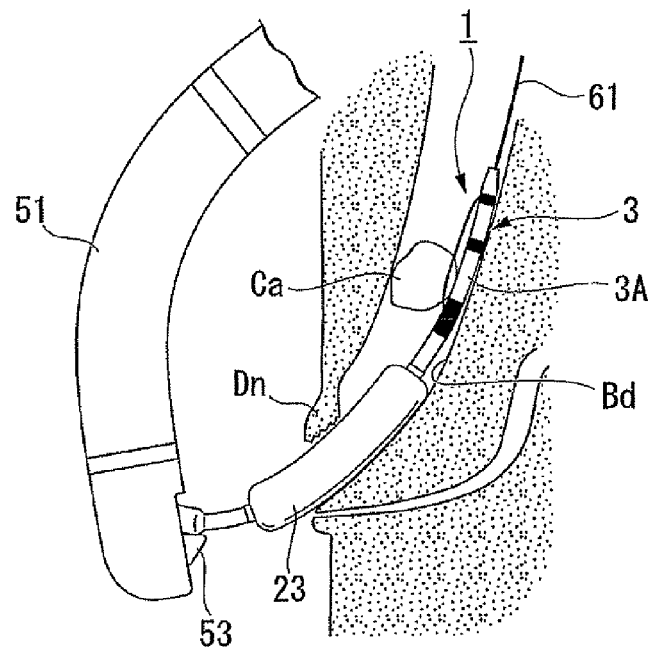
FIG. 10 is a diagram showing a state in which the papilla is pressed and enlarged by the balloon.

Here, saline or air is injected to the third lumen 13 from the syringe 41 connected to the first operation unit 39. The saline enters from each of the two holes 21 and 22 formed on the distal side of the third lumen 13 into the balloon 23 to swell the balloon 23. A pressure gauge is disposed between the syringe 41 and the first operation unit 39 to adjust an expansive pressure of the balloon 23. Since the diameter of the balloon 23 is changed in accordance with a pressure applied thereto, the balloon is pressurized up to a pressure necessary for a desired diameter. The expansive pressure may be a low pressure of 1 to 2 atmospheres since the papilla Dn is incised in advance. As shown in FIG. 10, the diameters of the papilla Dn and the bile duct Bd are further pressed and enlarged by the balloon 23.

Figure 11:
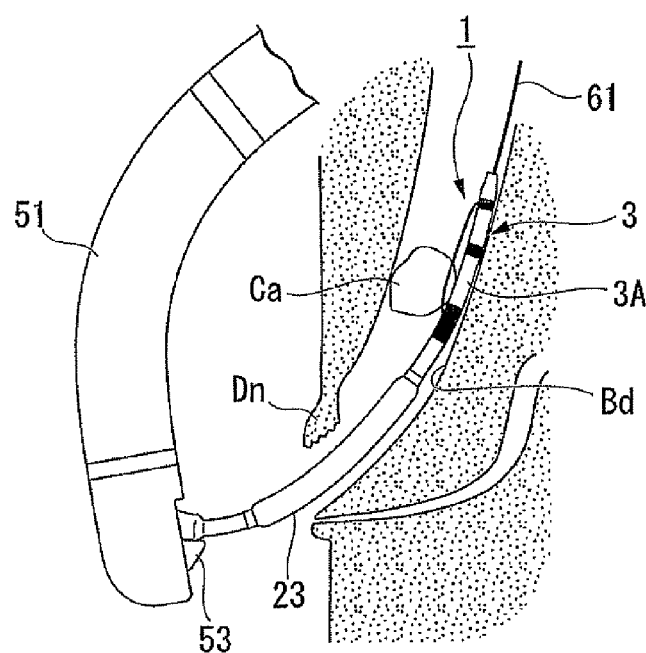
FIG. 11 is a diagram showing a state in which the balloon is shrunken after the process of FIG. 10.

Then, the saline or air injected into the balloon 23 is sucked out by the syringe 41. As shown in FIG. 11, the balloon 23 shrinks. The papilla Dn and the bile duct Bd are maintained in a state of enlargement.

Figure 12:
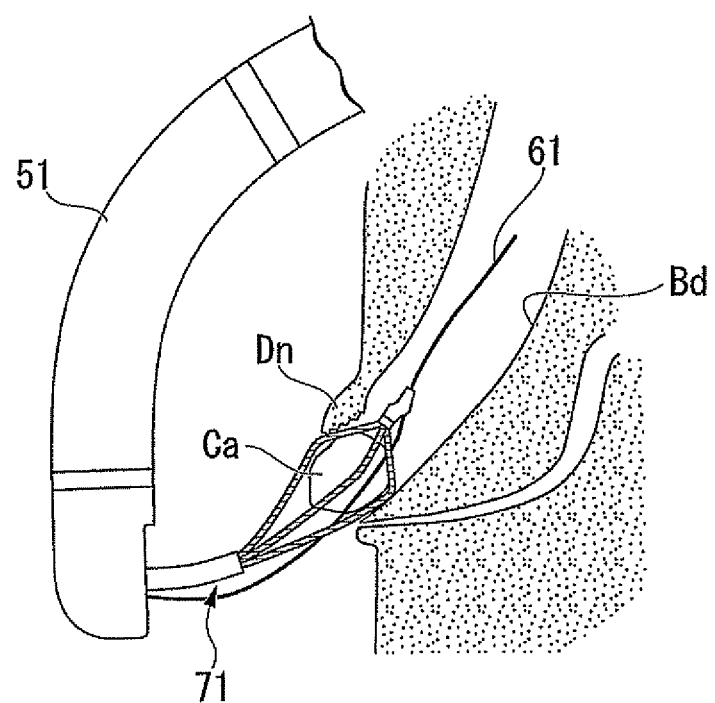
FIG. 12 is a diagram showing a state in which a calculus is discharged by a basket forceps.

In the state in which the guide wire 61 is left in the bile duct Bd, the papillotome 1 is removed to the outside the body. Alternatively, a basket forceps is inserted from the papilla Dn to the bile duct Bd through the work channel 52 of the endoscope 51. As shown in FIG. 12, a calculus Ca is captured by the basket forceps 71 and extracted from the bile duct Bd through the papilla Dn. Since an exit side of the bile duct Bd and the papilla Dn are enlarged in advance, the calculus Ca is easily extracted.

Further, the basket forceps 71 is configured to have a basket having a plurality of wires at the distal end of the flexible elongated sheath so as to freely project and retract. The plurality of wires are biased in advance so as to be enlarged in a basket shape when being allowed to project from the sheath, and distal ends thereof are bound together with a tip. The tip has a through hole, which is formed to allow passage of the guide wire 61, and can be easily inserted into the bile duct Bd along the guide wire 61.

When the calculus Ca is extracted, the endoscope 51 is taken out of the outside the body.

According to this embodiment, since the opening expansion by incision and the opening expansion by the balloon 23 can be realized with one medical instrument, a necessary opening diameter can be obtained without exchange of the medical instrument. Since the incision amount of tissue can be reduced, a possibility of bleeding can be reduced. Further, upon dilation to be caused by the balloon 23, compression of the tissue can be kept to a minimum. In addition, when only the dilation caused by the balloon is performed, as conventionally done, tissue around an exit of a pancreatic duct which is open to the papilla is strongly compressed. When this compression is too strong, the tissue around the pancreatic duct becomes swollen by inflammation, thereby blocking the exit of the pancreatic duct. Consequently, a possibility of pancreatitis increases. Since the tissue around the opening of the pancreatic duct must be strongly compressed, there are disadvantages in that a size expandable by a dilation balloon is limited and a size with which the calculus can be collected without destruction is smaller than in the case where the papilla is incised by the papillotome. For example, since a size expandable by a conventional balloon is about 8 mm, a size of the calculus to be collected without destruction is limited up to about 8 mm. However, according to this embodiment, the bile duct exit and the pancreatic duct exit can be disposed apart from each other with the incision of the papillotome before expansion of the papilla, and the compression to the tissue around the pancreatic duct exit upon expansion can be reduced. Accordingly, the expansion can be performed on a large scale, and a large calculus can be collected.

Since the balloon 23 is configured such that the length in the axial direction is larger than the expansive diameter, displacement in pressing and enlargement of the channel is controlled and a desired site can be securely expanded.

In the past, in the case of size requiring fragmentation by ESWL, there were disadvantages in that an invasion to a patient increases, a period of treatment or procedure is lengthened, or a medical fee increases, due to the complicated procedure. However, according to this embodiment, it is possible to extract even a relatively large calculus as it is, and thus it is possible to simplify the procedure and shorten the period of treatment or procedure.

Since the two holes 21 and 22 are provided at a front portion and a rear portion in the third lumen 13, the balloon 23 can be rapidly expanded or shrunken. Particularly, even in the case where the balloon 23 is in close contact with one of the holes 21 and 22 in the step of shrinking the balloon 23, the balloon 23 can be securely shrunken since fluid can be discharged from the other of the holes 21 and 22. In this way, the expansion and the shrinkage of the balloon 23 are continuously performed even in the case where one long hole is provided instead of the two holes 21 and 22 as described above. When the fluid is drained from the balloon 23, the balloon can be securely shrunken since the fluid can be discharged from the other end of the long hole.

Here, the balloon 23 may be made of a non-elastomeric material. As the non-elastomeric material, polyurethane, polyethylene, polyamide, PET (polyethylene terephthalate), or the like, which is low in stretching property but is high in resistance to pressure, is used. In this case, the largest expansive diameter of the balloon 23 is about 16 mm to 20 mm, and the length in the longitudinal direction thereof is 1.5 to 2 times the largest expansive diameter (specifically, 30 mm to 40 mm).

Since the non-elastomeric material is low in stretching property, the expansive diameter of the balloon 23 can be adjusted with a relatively high accuracy by adjusting the expansive pressure with hand. For example, the expansive diameter can be adjusted to 16 mm at a pressure of 1 atmosphere, to 18 mm at a pressure of 2 atmospheres, and to 20 mm at a pressure of 3 atmospheres. Accordingly, the expansive diameter can be arbitrarily changed by one papillotome 1 in response to a medical case, such that the expansive pressure is adjusted by the pressure gauge in hand to expand the balloon up to 16 mm when the calculus is not too large and to expand the balloon up to 20 mm when the calculus is large.

A relationship between the expansive pressure and the expansive diameter can be arbitrarily changed by changing the kind of the non-elastomeric material. For example, when a material having a higher stretching property is used, the diameter can be largely changed with a small difference in pressure such that the diameter is adjusted to 16 mm at a pressure of 1 atmosphere, to 18 mm at a pressure of 1.5 atmospheres, and to 20 mm at a pressure of 2 atmospheres. In this case, it is not necessary to use a screw type or expensive inflake with a booster mechanism, a desired expansive diameter can be obtained by a cheap syringe having a simple configuration, and a cost can be thereby reduced.

On the other hand, when a material having a small stretching property, such as PET, is used, a design can be made such that a substantially constant diameter, for example 18 mm, is maintained at a pressure of 1, 2, and 3 atmospheres. When the expansive diameter is adjusted to be constant over the wide pressure range, it is not necessary to accurately adjust the pressure. Since the balloon 23 can be swollen to a desired size without the pressure gauge, a cost can be reduced.

Figure 13:
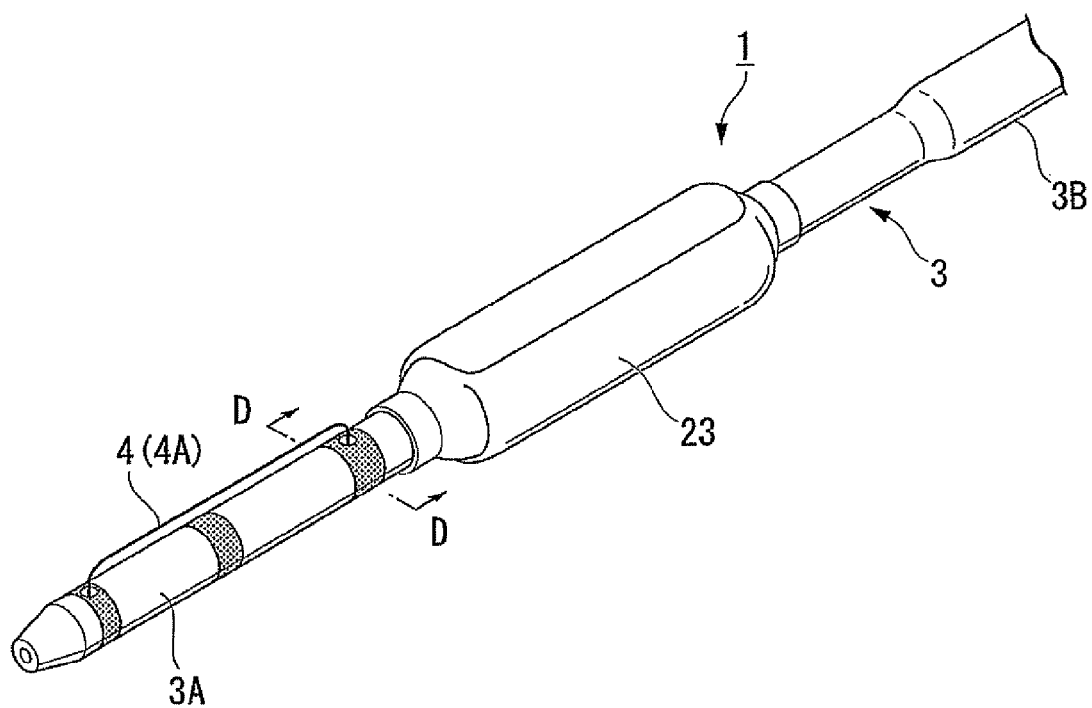
FIG. 13 is an appearance diagram when the balloon is made of a non-elastomeric material.
Figure 14:
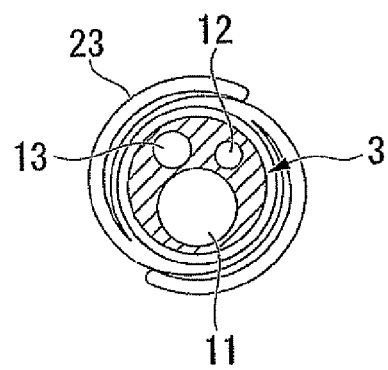
FIG. 14 is a cross-sectional view taken along the line D-D of FIG. 13.

Furthermore, as shown in FIG. 13, when the balloon is made of a non-elastomeric material, the distance between the incision knife portion 4A and the distal end of the balloon 23 is narrower than the aforementioned case, for example, the distance is 0.5 to 1.5 cm. As shown in FIGS. 13 and 14, the outer diameter of the balloon 23 upon shrinkage is reduced by winding the balloon around the outer circumference of the sheath 3.

Second Embodiment

Figure 15:
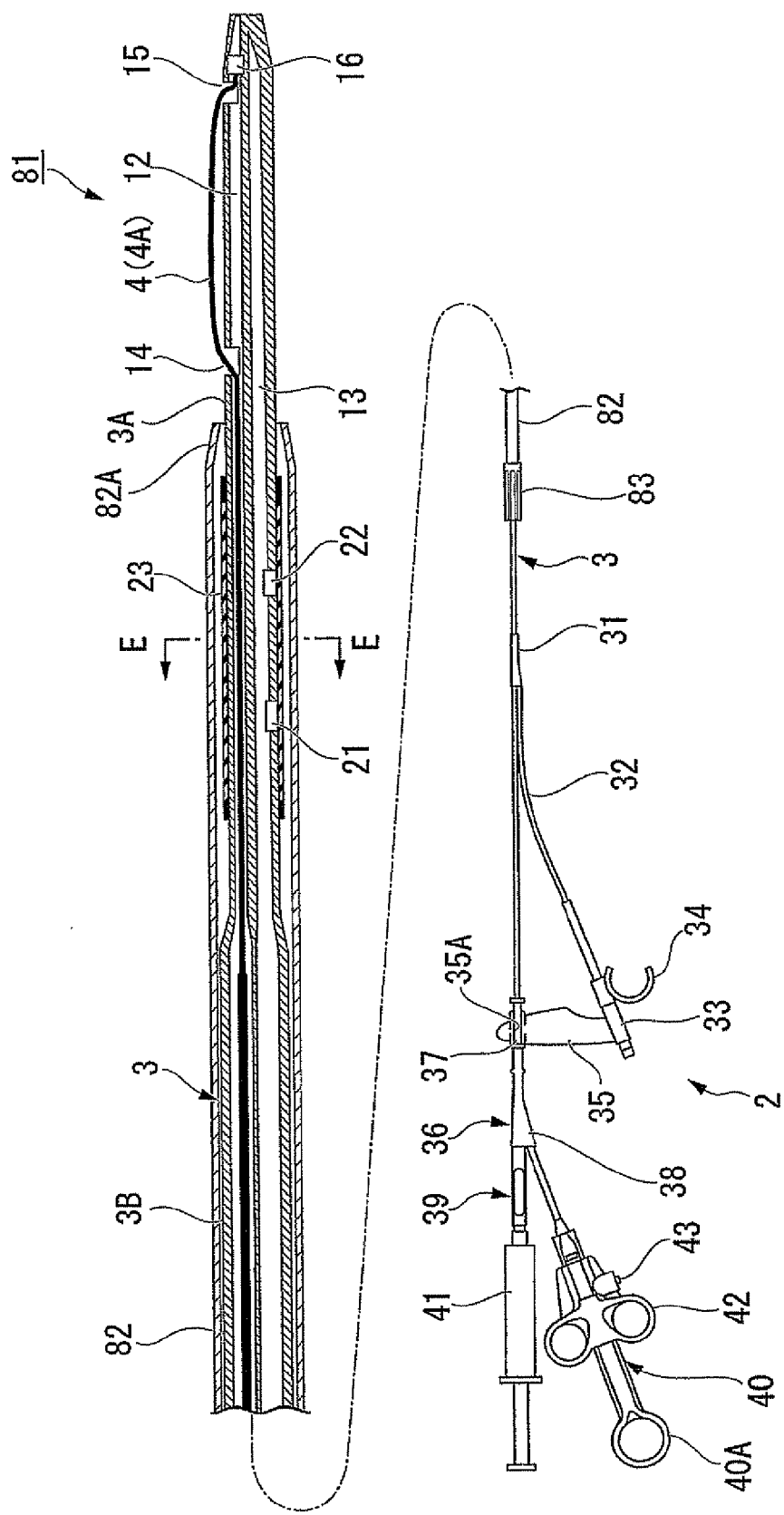
FIG. 15 is a diagram showing the configuration of a papillotome which is an example of a medical instrument for an endoscope and has a cover sheath.
Figure 16:
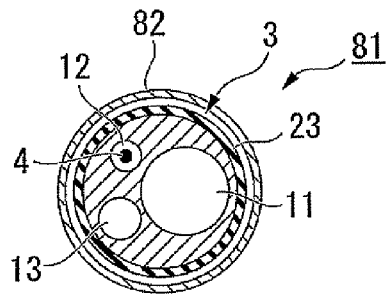
FIG. 16 is a cross-sectional view taken along the line E-E of FIG. 15.

FIGS. 15 and 16 show the configuration of a papillotome which is an example of a medical instrument for an endoscope. The papillotome 81 has a characteristic in that a cover sheath 82 covers the outside of a sheath 3 so as to advance and retreat.

The cover sheath 82 is elongated and flexible. A grip 83 is attached to a portion, which is drawn out of a proximal end of the cover sheath 82 to the outside, so as to be easily gripped by an operator. The cover sheath 82 has an inner diameter which is larger than the outer diameter of a balloon upon shrinkage and a thick portion 3B of the sheath 3. In an initial state, a distal end of the cover sheath is disposed so as to cover the whole balloon 23 and to expose an incision knife portion 4A. Further, a distal portion 82A of the cover sheath 82 is reduced in diameter in a tapered shape so as to be easily inserted into a papilla Dn.

A distance between the balloon 23 and the incision knife portion 4A is shorter than that of the first embodiment, and both of them are relatively close to each other. The balloon 23 is made of the elastomeric material or the non-elastomeric material described in the first embodiment.

Figure 17:
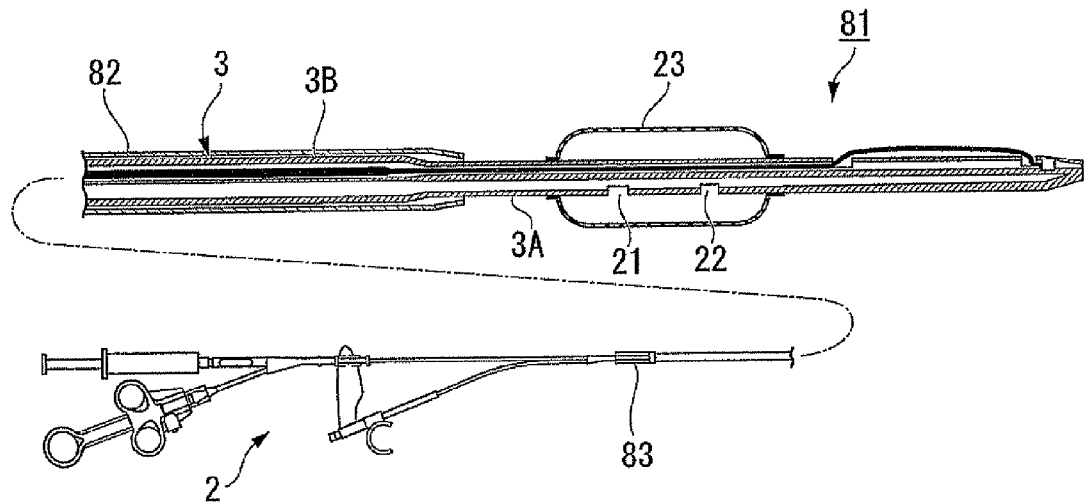
FIG. 17 is a diagram showing a state in which the cover sheath is retreated to swell a balloon.

As shown in FIG. 17, when a knob 82 is gripped to push an operating portion 2, and the balloon 23 is completely exposed from the cover sheath 82 and then is swollen, the balloon 23 can be entirely swollen. The balloon 23 becomes slender in the longitudinal direction of the sheath 3, and the length in the axial direction thereof is larger than the expansive diameter.

Figure 18:
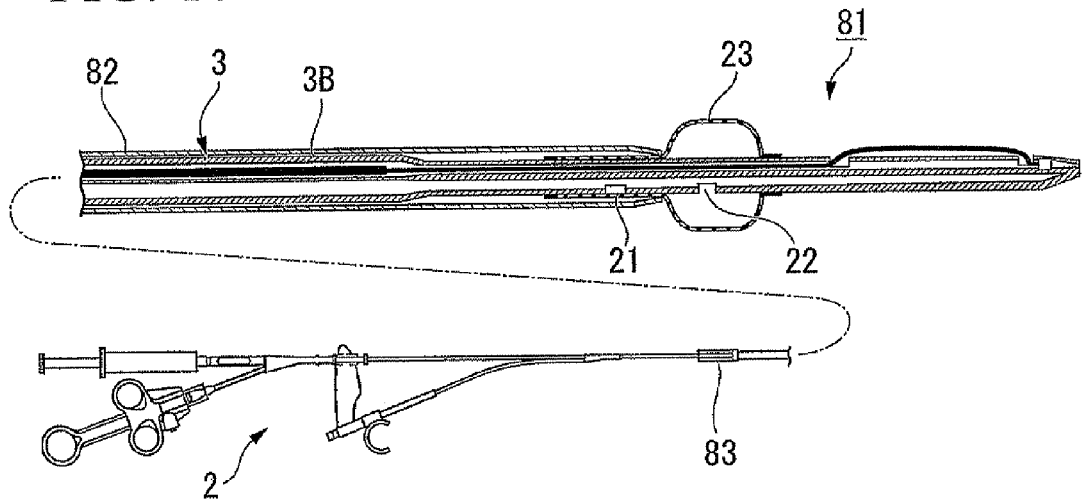
FIG. 18 is a diagram showing a state in which the cover sheath is advanced to swell only a distal portion of the balloon.

However, as shown in FIG. 18, when the distal end of the cover sheath 82 is disposed in the vicinity of the center in the longitudinal direction of the balloon 23, that is, between two holes 21 and 22, or disposed in the middle of the one long hole as an alternative to the two holes 21 and 22, and the balloon 23 is then swollen, it is possible to swell only the distal portion of the balloon, which is exposed from the cover sheath 82. Since the expansion of the proximal portion of the balloon 23 is suppressed by the cover sheath 82, there is no case where the balloon is more swollen than the cover sheath 82. At this time, the balloon 23 is swollen such that the length in the longitudinal direction of the sheath 3 is short.

Next, a procedure using the papillotome 81 will be described.

Figure 19:
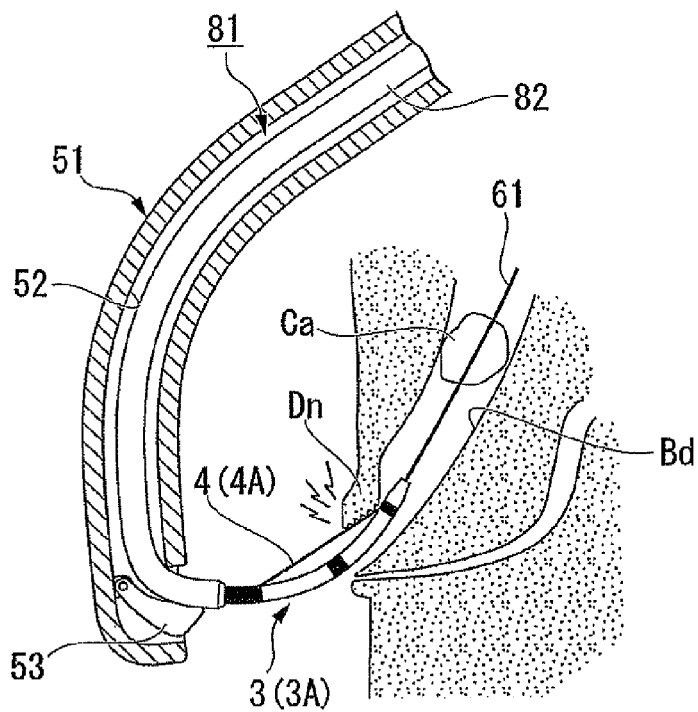
FIG. 19 is a diagram showing a state in which a papilla is incised by the papillotome shown in FIG. 17.
Figure 20:
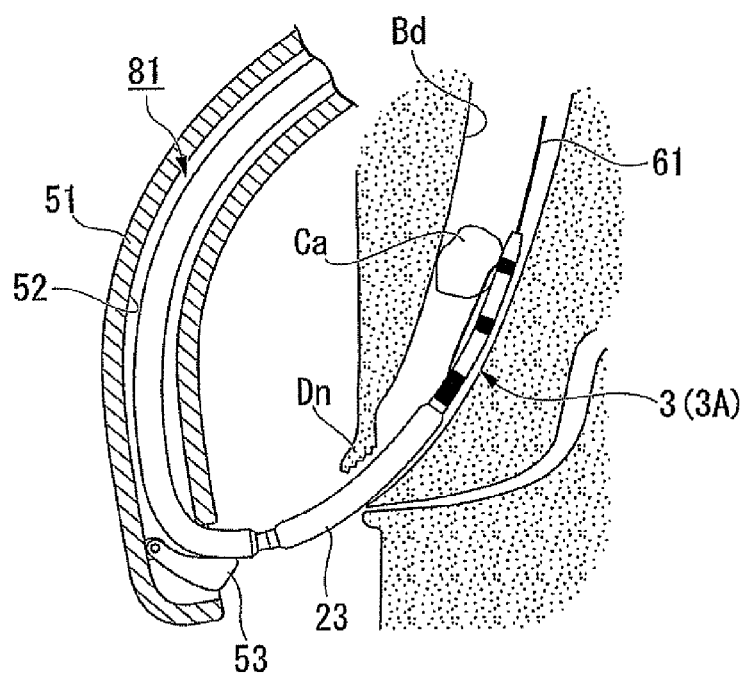
FIG. 20 is a diagram showing a state in which the exposed balloon is inserted up to the papilla.

In a state in which the balloon 23 is covered with the cover sheath 82, the papillotome 81 passes through an endoscope. As shown in FIG. 19, while the incision knife portion 4A is stretched in an arc shape and supplied with radio-frequency current, an erecting base 53 is operated to incise the papilla Dn. An incision amount is the same as that described above. As shown in FIG. 20, the sheath 3 is inserted from the papilla Dn to a bile duct Bd. At this time, the grip 83 on a hand side is gripped to be fixed, and the sheath 3 is pushed to advance. Since the sheath 3 advances relatively in a state in which the cover sheath 82 is not moved, the balloon 23 is exposed. The papillotome 81 advances such that, for example, the center in the axial direction of the balloon 23 reaches to the papilla Dn.

Figure 21:
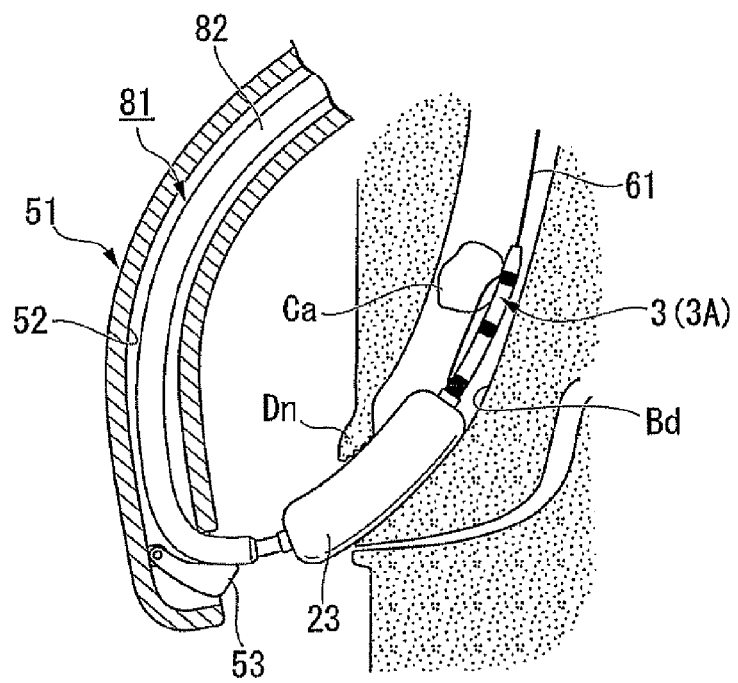
FIG. 21 is a diagram showing a state in which the balloon is swollen to press and enlarge the papilla.
Figure 22:
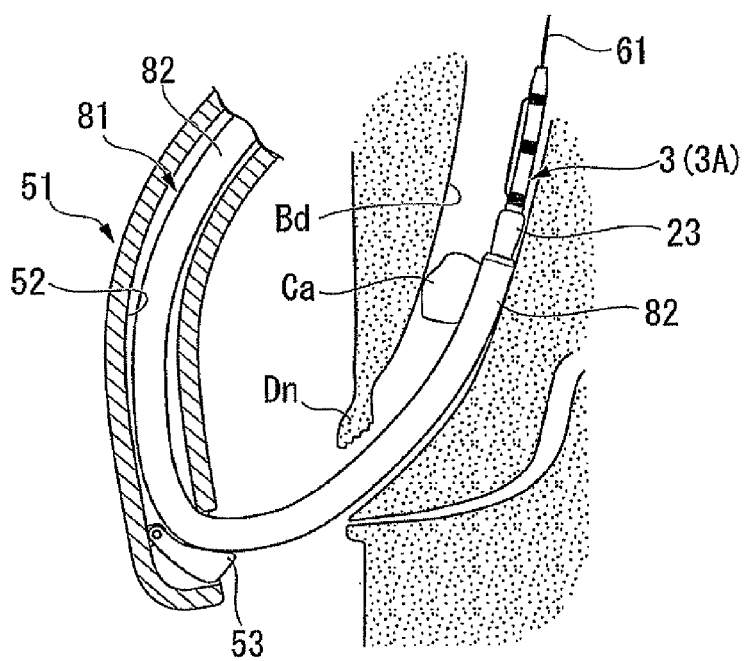
FIG. 22 is a diagram showing a state in which the cover sheath is advanced and the papillotome is advanced such that substantially one half of the balloon is hidden.

As shown in FIG. 21, the balloon 23 is entirely swollen to enlarge the papilla Dn and the exit side of the bile duct 13d. And then, the balloon 23 is shrunken. Furthermore, as shown in FIG. 22, the cover sheath 82 is advanced to accommodate the proximal portion of the balloon 23 (a portion including the hole 21 on the proximal side, or a portion including the proximal side of the one long hole as the alternative to the two holes 21 and 22) in the cover sheath 82. At this time, the papillotome 81 is advanced such that the exposed portion of the balloon 23 is disposed deeper than a calculus Ca.

Figure 23:
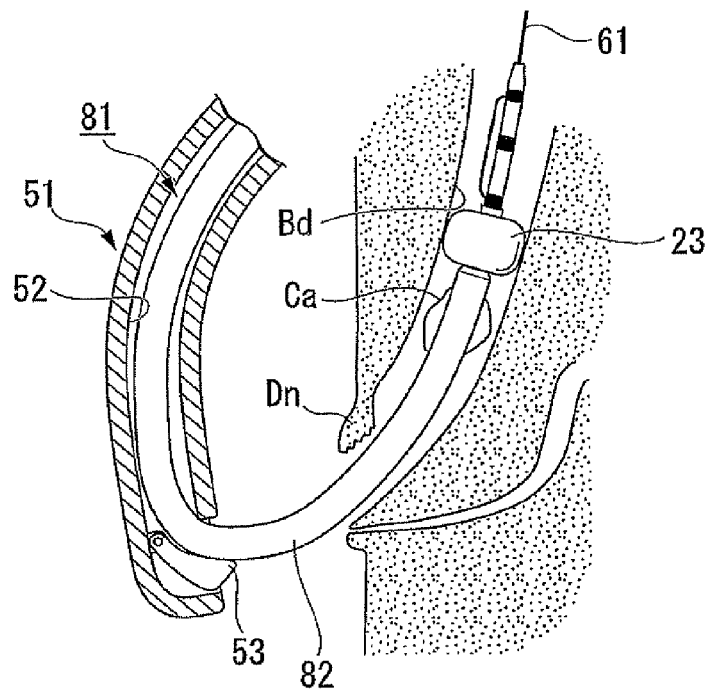
FIG. 23 is a diagram showing a state in which the balloon exposed from the cover sheath is swollen.
Figure 24:
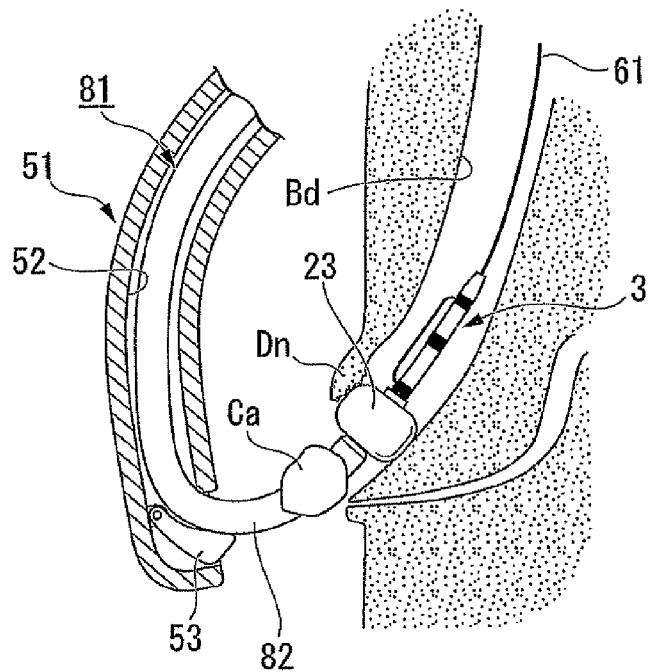
FIG. 24 is a diagram showing a state in which a calculus is scraped out by the balloon.

As shown in FIG. 23, when the balloon 23 is expanded, the balloon 23 is swollen so as to block up the bile duct Bd on a back side of the calculus Ca. A volume of the balloon 23 is about one half of an initial volume thereof. In this state, the cover sheath 82 and the sheath 3 are pulled together. As shown in FIG. 24, the calculus Ca is discharged from the bile duct Bd so as to be scraped out by the balloon 23.

According to this embodiment, since the cover sheath 82 is provided, a shape of the balloon 23 when being swollen can be changed. When the balloon 23 is entirely swollen, a large area of tissue can be pressurized, and a desired site of the channel can be securely expanded without displacement. However, when the length in the axial direction of the balloon 23 to be expanded by the cover sheath 82 is reduced and only the distal portion is swollen, the length in the axial direction is shortened, and thus the balloon becomes easy to move along a curved shape of the bile duct Bd. Accordingly, the calculus Ca is easily discharged by the balloon 23. Since the need for exchanging the papillotome 81 with a medical instrument for discharge a calculus is eliminated, a period of procedure can be reduced and a burden of a patient can be reduced.

Third Embodiment

Figure 25:
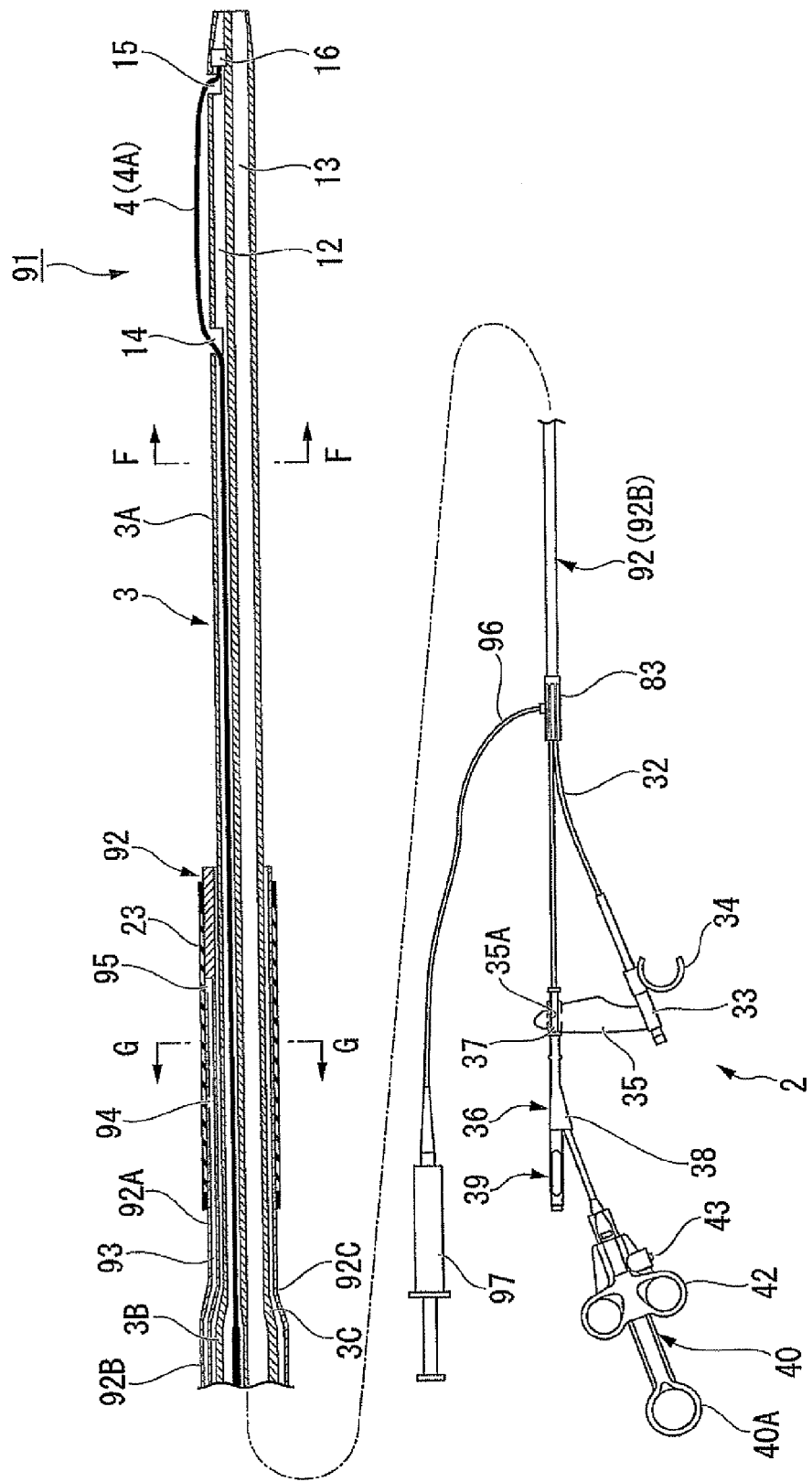
FIG. 25 is a diagram showing the configuration of a papillotome in which a cover sheath is provided with a balloon.

FIG. 25 shows the configuration of a papillotome which is an example of a medical instrument for an endoscope. The papillotome 91 has a characteristic in that a balloon 23 is attached to a cover sheath 92 covering the outside of a sheath 3.

Figure 26:
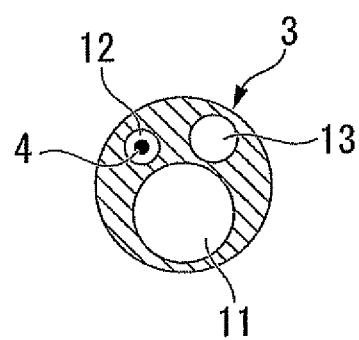
FIG. 26 is a cross-sectional view taken along the line F-F of FIG. 25.
Figure 27:
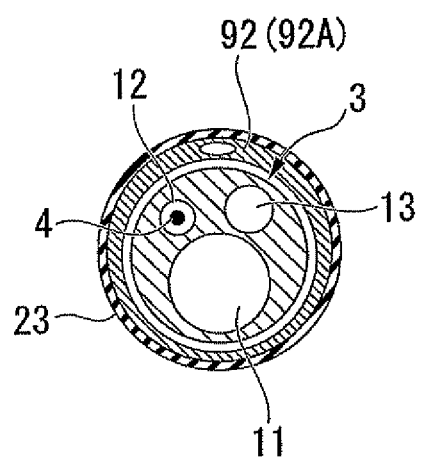
FIG. 27 is a cross-sectional view taken along the line G-G of FIG. 25.

As shown in FIGS. 26 and 27, the sheath 3 has three lumens 11, 12 and 13. A guide wire 61 passes through the first lumen 11A and the conductive wire 4 passes through the second lumen 12. The third lumen 13 has an opening formed at a distal end thereof. A contrast agent is ejected from a distal end of the sheath 3 when a syringe is mounted on a mouth ring of a first operation unit 39 on a hand side.

Figure 28:
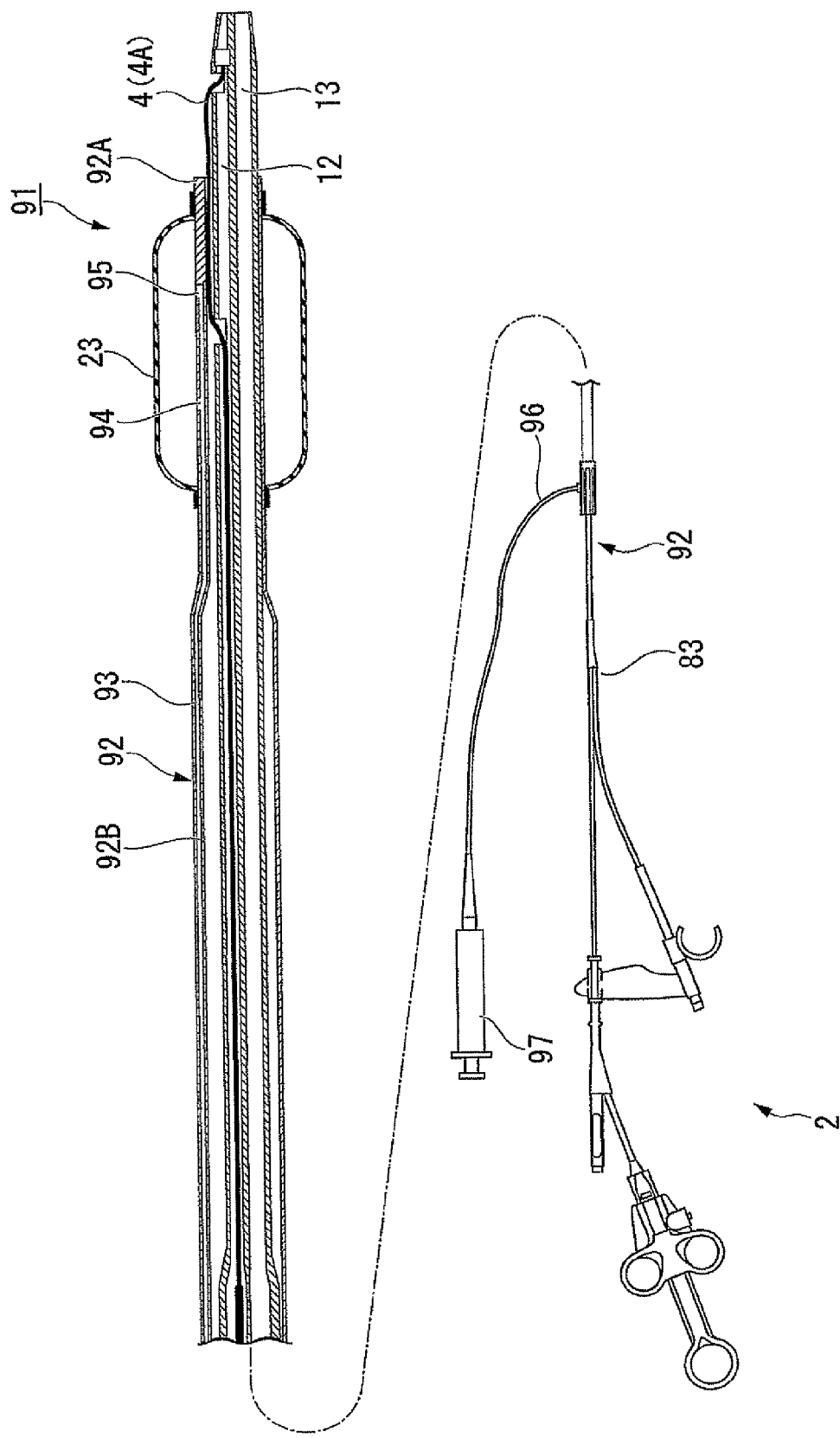
FIG. 28 is a diagram showing a state in which the cover sheath is advance to swell the balloon.

The cover sheath 92 has an inner diameter which is larger than that of a thick portion 3B of the sheath 3, and has a balloon mounting portion 92A which is formed to mount the balloon 23 at the distal end. The balloon mounting portion 92A is thinner than the other portion 92B in accordance with the change in diameter of the sheath 3. In the cover sheath 92, a lumen 93 for passing fluid therethrough is formed. The lumen 93 is open to a side surface through two holes 94 and 95. The balloon 23 is attached to the cover sheath 92 so as to cover the holes 94 and 95. The material and the shape of the balloon 23 are the same as in the above-described embodiments. The two holes 94 and 95 are disposed at positions defined by dividing a length in the axial direction of the balloon 23 into substantially three equal parts. The lumen 93 extends up to a proximal portion of the cover sheath 92, and is connected to the syringe 97 through a tube 96 from a grip 83. When fluid such as saline or air is supplied from the syringe 97, the balloon 23 can be swollen, as shown in FIG. 28.

In addition, a length of the cover sheath 92 is set such that the distal end of the sheath 3 matches with the distal end of the cover sheath 92 when the cover sheath 92 is advanced to the end. Further, the cover sheath 92 can be retreated such that a proximal portion 92C of the balloon mounting portion 92A, which is reduced in diameter, collides with a step portion 3C which is formed by reducing the diameter of the sheath 3. A portion 3A of the sheath 3, which is reduced in diameter, is formed up to a position where the cover sheath 92 can be retreated to the hand side such that the balloon 23 is not caught by the erecting base upon insertion to a papilla and incision of the papilla.

Next, a procedure using the papillotome 91 will be described.

Figure 29:
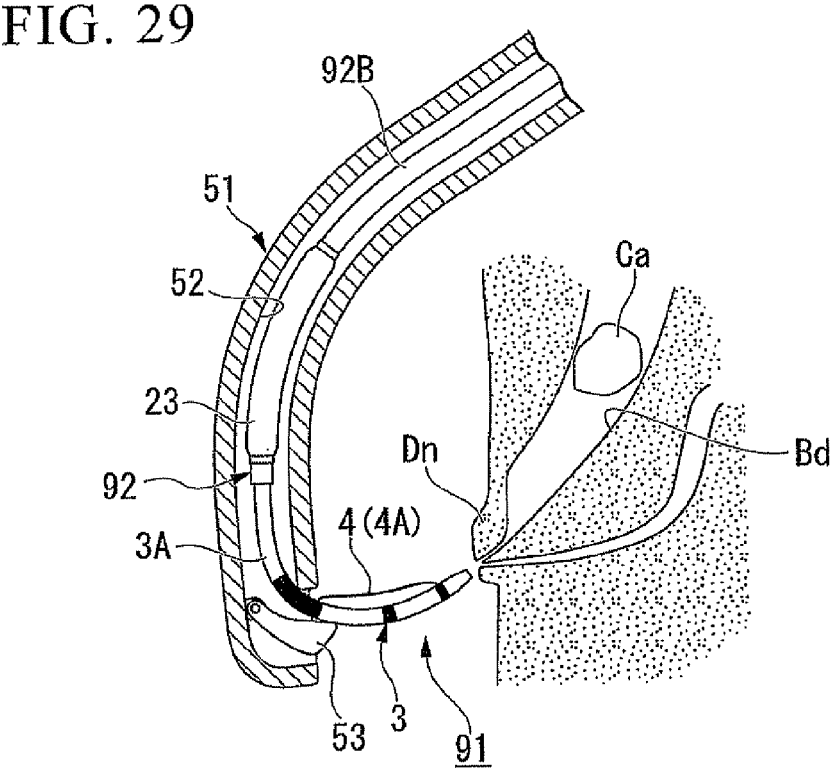
FIG. 29 is a diagram showing a use pattern of the papillotome of FIG. 25.
Figure 30:
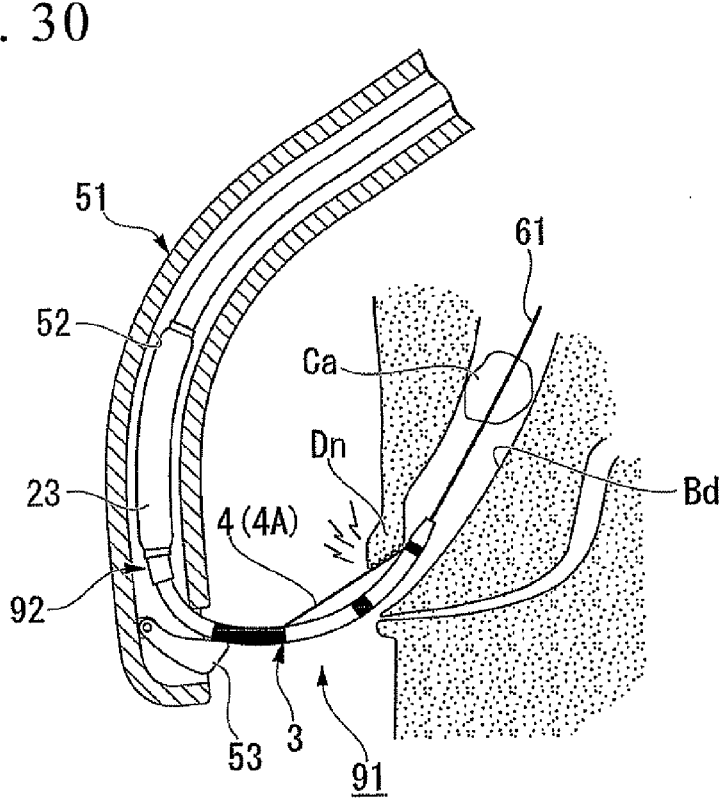
FIG. 30 is a diagram showing a state in which a papilla is incised by an incision knife portion.

As shown in FIG. 29, in a state in which the cover sheath 92 is retreated to expose the distal portion 3A of the sheath 3, the sheath 3 is pushed by the erecting portion 53 to approach the papilla Dn. As shown in FIG. 30, a predetermined amount of the papilla Dn is incised by an incision knife portion 4A of the conductive wire 4 stretched in an arc shape.

Figure 31:
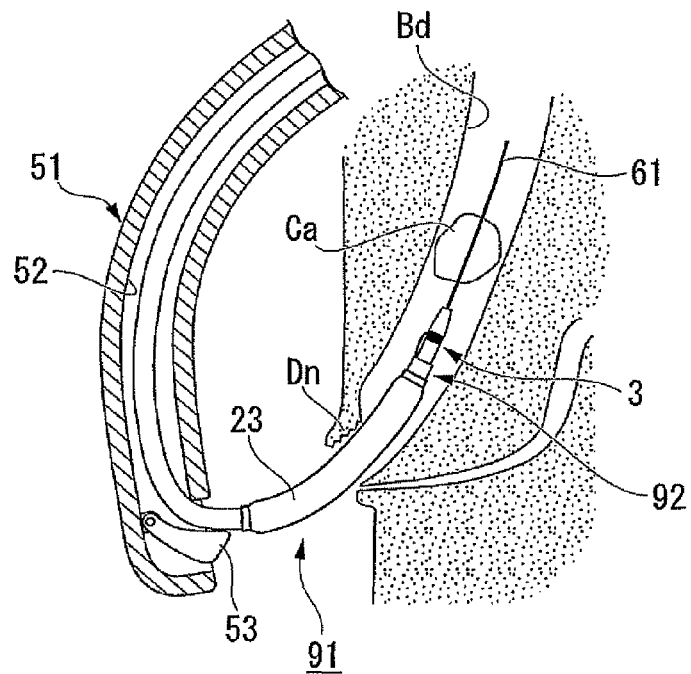
FIG. 31 is a diagram showing a state in which the cover sheath is advanced to insert the balloon up to the papilla.
Figure 32:
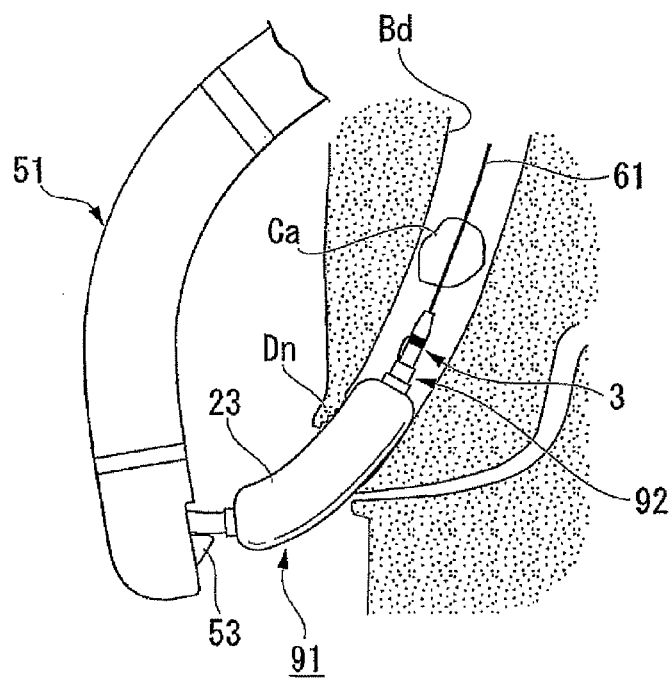
FIG. 32 is a diagram showing a state in which the balloon is swollen to press and enlarge the papilla.

When the papilla Dn and the exit of a bile duct Bd are enlarged by the balloon 23, only the cover sheath 92 is advanced, as shown in FIG. 31. For example, the cover sheath 92 is advanced such that the center of the balloon 23 reaches to the papilla Dn. At this time, the sheath 3 is not advanced. When saline or air is injected from the syringe 97 on the hand side, the balloon 23 is swollen through the lumen 93 in the cover sheath 92, and as shown in FIG. 32, the papilla Dn and the exit side of the bile duct Bd are pressed and enlarged.

After that, the balloon 23 is shrunken. In the state in which the guide wire 61 is left, the papillotome 91 is removed. Alternatively, a basket forceps or the like is inserted and a calculus Ca is collected.

According to this embodiment, the balloon 23 is attached to the cover sheath 92 which advances and retreats relative to the sheath 3 holding the incision knife portion 4A. Since the cover sheath 92 can advance up to a position where the balloon 23 overlaps the incision knife portion 4A, the papilla Dn and the exit side of the bile duct Bd can be enlarged with no need for deeply advancing the papillotome 91 into the bile duct Bd.

Fourth Embodiment

Figure 33:
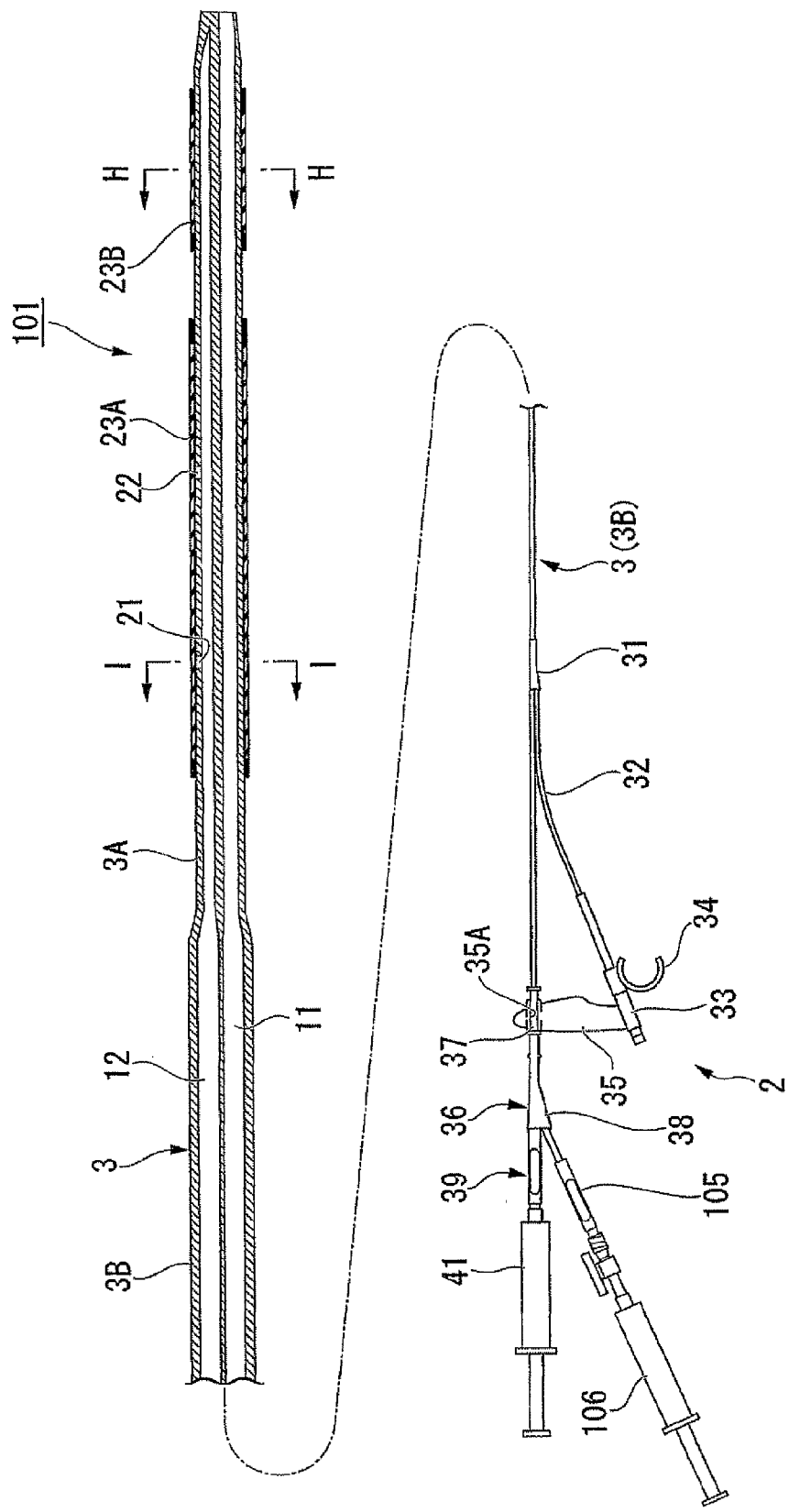
FIG. 33 is a diagram showing the configuration of a medical instrument for an endoscope having two balloons.

FIG. 33 shows the configuration of a medical instrument for an endoscope. The medical instrument for an endoscope 101 does not have the conductive wire described in the above-described embodiments. Alternatively, two balloons are mounted.

The medical instrument for an endoscope 101 (hereinafter, referred to as medical instrument) has a flexible and elongated sheath 3 with an operating portion 2 attached to the proximal end of the sheath 3.

Figure 34:
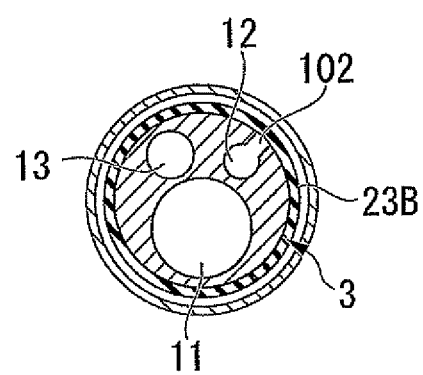
FIG. 34 is a cross-sectional view taken along the line H-H of FIG. 33.
Figure 35:
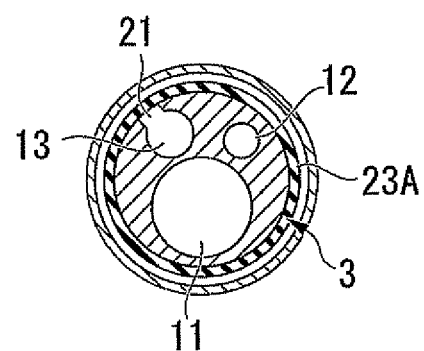
FIG. 35 is a cross-sectional view taken along the line I-I of FIG. 33.

The sheath 3 is flexible. A distal portion 3A reduced in diameter is mounted with a first balloon 23A and a second balloon 23B which are disposed at a front portion and a rear portion in the axial direction. As shown in FIGS. 34 and 35, among three lumens 11 to 13 formed in the sheath 3, the first lumen 11 is open at a distal end thereof and has a guide wire passing therethrough or used to inject a contrast agent thereto. The second lumen 12 has the smallest diameter and communicates with the second balloon 23B on the distal end through a hole 102. The hole 102 is disposed about midway between fixing portions at both ends in the axial direction of the second balloon 23B. The third lumen 13 is thicker than the second lumen 12, and has two holes 21 and 22 which communicate with the first balloon 23A and are substantially disposed at a front portion and a rear portion in the axial direction. The holes 21 and 22 are disposed at positions defined by dividing a distance between the fixing portions at the both ends in the axial direction of the first balloon 23A into substantially three equal parts. Instead of the two holes 21 and 22, one long hole including the positions of the two holes may be provided. Fluid easily flows since the third lumen 13 is thicker than the second lumen 12. The first balloon 23A having a large volume can be rapidly swollen and shrunken.

Figure 36:
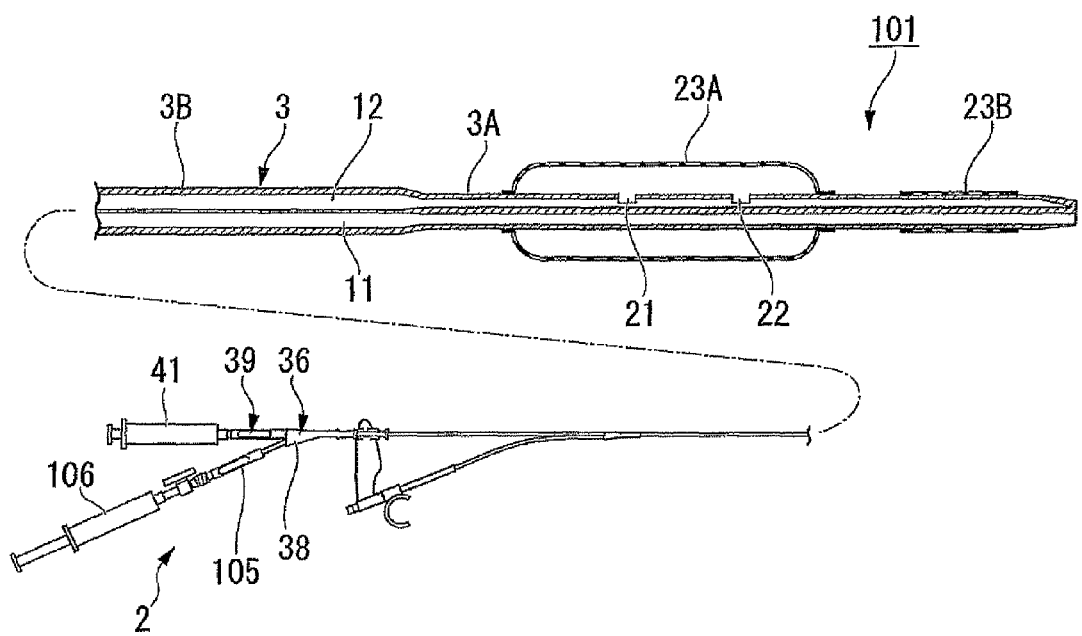
FIG. 36 is a diagram showing a state in which the balloon of a proximal side is swollen.
Figure 37:
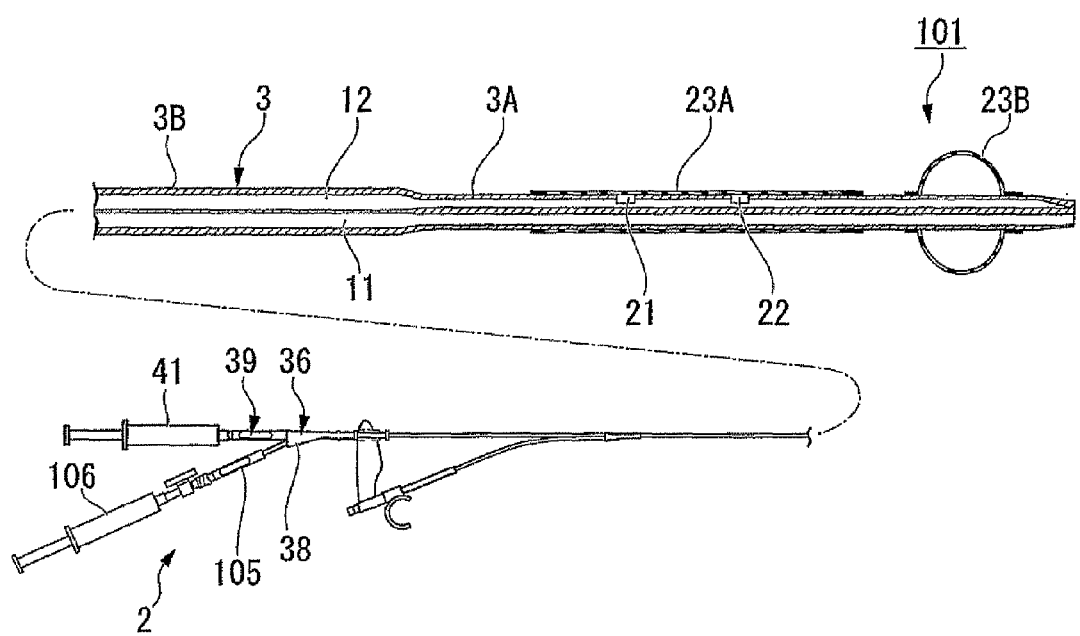
FIG. 37 is a diagram showing a state in which the balloon of a distal side is swollen.

Here, as shown in FIGS. 33 and 36, the shape and the size of the first balloon 23A as a dilator are the same as in the first and second embodiments. The second balloon 23A is a small balloon which is disposed on the distal side and of which a length in the axial direction is shorter than that of the first balloon 23A, for example, about one half of the first balloon 23A. The material for each of the balloons 23A and 23B is the same as in the above-described embodiment. The shape and the size of the second balloon 23B are the substantially same as those of the balloon swollen on only the distal side thereof in the second embodiment.

In the operating portion 2, a second operation unit 105 has a mouth ring and a syringe 106 with a valve is removably disposed.

Next, a procedure using the medical instrument 101 will be described.

Figure 38:
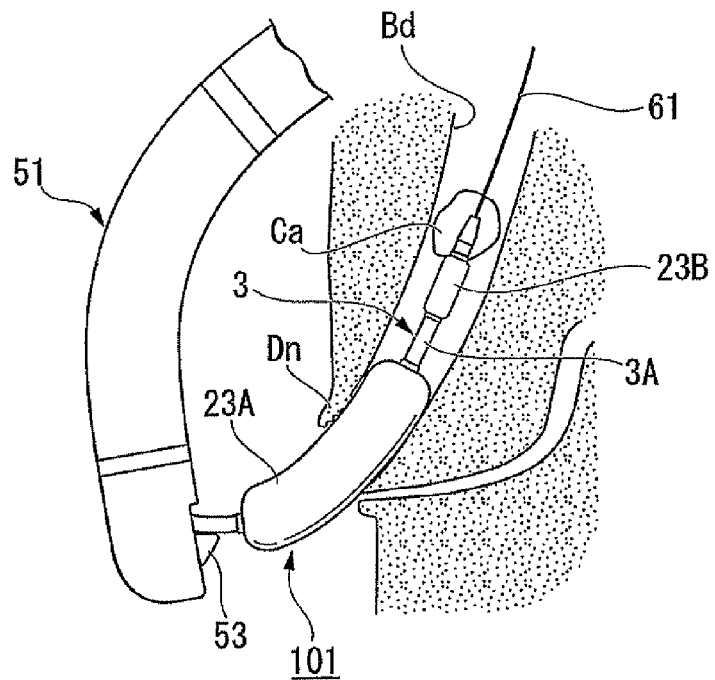
FIG. 38 is a diagram showing a state in which the balloon of the proximal side is swollen to press and enlarge a papilla.

After a papilla Dn is incised by a radio-frequency knife (not shown) and an opening is enlarged, the medical instrument 101 is introduced from the papilla Dn to a bile duct Bd along the guide wire 61. The medical instrument 101 is advanced such that a substantial center of the first balloon 23A reaches to the papilla Dn. As shown in FIG. 38, when the first balloon 23A is swollen, the papilla Dn and the exit of the bile duct Bd are enlarged. At this time, fluid is supplied only from a syringe 41 of a first operation unit 39. The first balloon 23A is injected with the fluid from each of the two holes 21 and 22 through the third lumen 13, and thereby swollen.

Then, the fluid is drained from the first balloon 23A to shrink the balloon. Since the fluid is drained through the two holes 21 and 22, the fluid is securely removed for shrinkage even in the case where the balloon 23A is in close contact with one of the holes 21 and 22 or where the balloon 23A is in close contact with one end of the long hole. Subsequently, the medical instrument 101 is further advanced into the back of the bile duct Bd. The medical instrument 101 allows the second balloon 23B to be advanced deeper than a calculus Ca.

Figure 39:
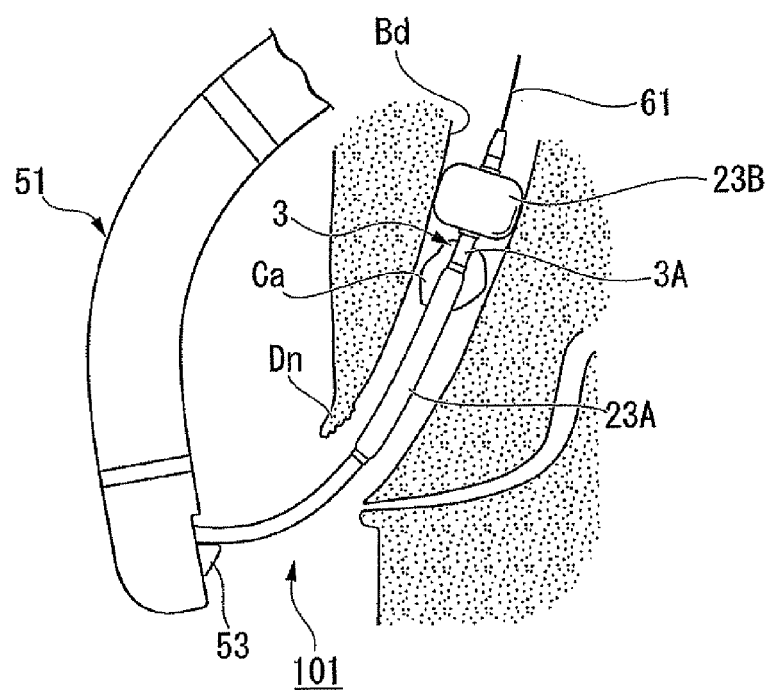
FIG. 39 is a diagram showing a state in which the balloon of the proximal side is swollen in the rear of a calculus.

As shown in FIG. 39, the second balloon 23B is swollen. The second balloon 23B is supplied with fluid from the syringe 106 mounted on a mouth ring of the second operation unit 105, and thereby swollen. Since the second balloon 23B is swollen so as to block up the bile duct Bd, the valve of the syringe 106 is closed so as not to shrink the second balloon 23B, and the medical instrument 101 is then retreated. The calculus Ca is discharged from the bile duct Bd so as to be scraped out by the second balloon 23B.

According to this embodiment, since the two balloons 23A and 23B, which are different from each other in position and size, are provided, the expansion of the channel and the discharge of the calculus Ca are securely performed. By the first balloon 23A, a large area of tissue can be pressurized, and a desired site of the channel can be securely expanded without displacement. The second balloon 23B is shortened in the axial direction so as to easily move along an arc shape of the bile duct Bd. Accordingly, the calculus Ca is easily discharged. Since the second balloon 23B is provided on the distal side, an insertion amount of the medical instrument 101 is small. A period of procedure can be reduced and a burden of a patient can be reduced.

Fifth Embodiment

Figure 40:
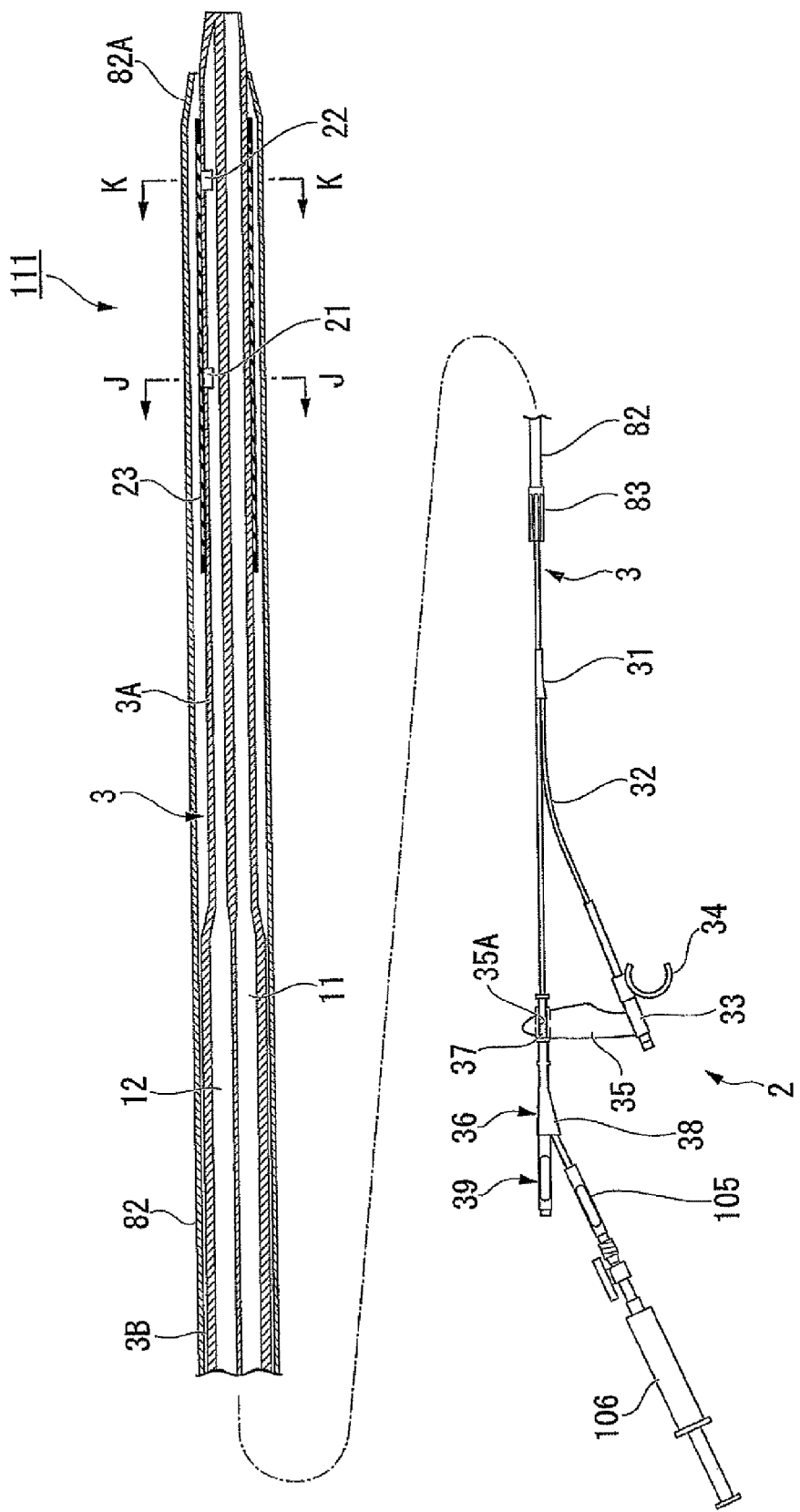
FIG. 40 is a diagram showing the configuration of a medical instrument for an endoscope having one balloon and a cover sheath.

FIG. 40 shows the configuration of a medical instrument for an endoscope. The medical instrument for an endoscope 111 does not have a conductive wire but a balloon and a cover sheath.

The medical instrument for an endoscope 111 (hereinafter, referred to as medical instrument) has a flexible and elongated sheath 3 with an operating portion 2 attached to the proximal end of the sheath 3.

Figure 41:
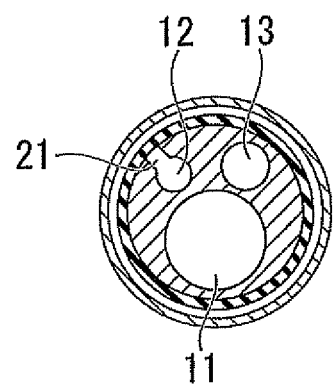
FIG. 41 is a cross-sectional view taken along the line J-J of FIG. 40.
Figure 42:
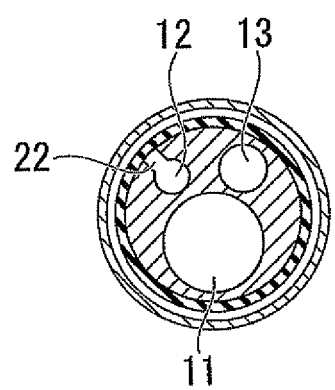
FIG. 42 is a cross-sectional view taken along the line K-K of FIG. 40.

As shown in FIGS. 40, 41 and 42, the balloon 23 is mounted on a distal portion 3A of the flexible sheath 3, which is small in diameter. Two holes 21 and 22 allowing the balloon 23 to communicate with a second lumen 12 are formed at a front portion and a rear portion in the axial direction. The holes 21 and 22 are substantially disposed at positions defined by dividing a distance between fixing portions at both ends in the axial direction of the balloon 23 into three. Instead of the two holes 21 and 22, the one long including the positions of the two holes may be provided. In the operating portion 2, a second operation unit 105 is provided with a mouth ring and a syringe 106 with a valve is removably disposed. The second operation unit 105 communicates with the second lumen 12. The shape and the size of the balloon 23 are the same as in the first and second embodiment.

Figure 43A:
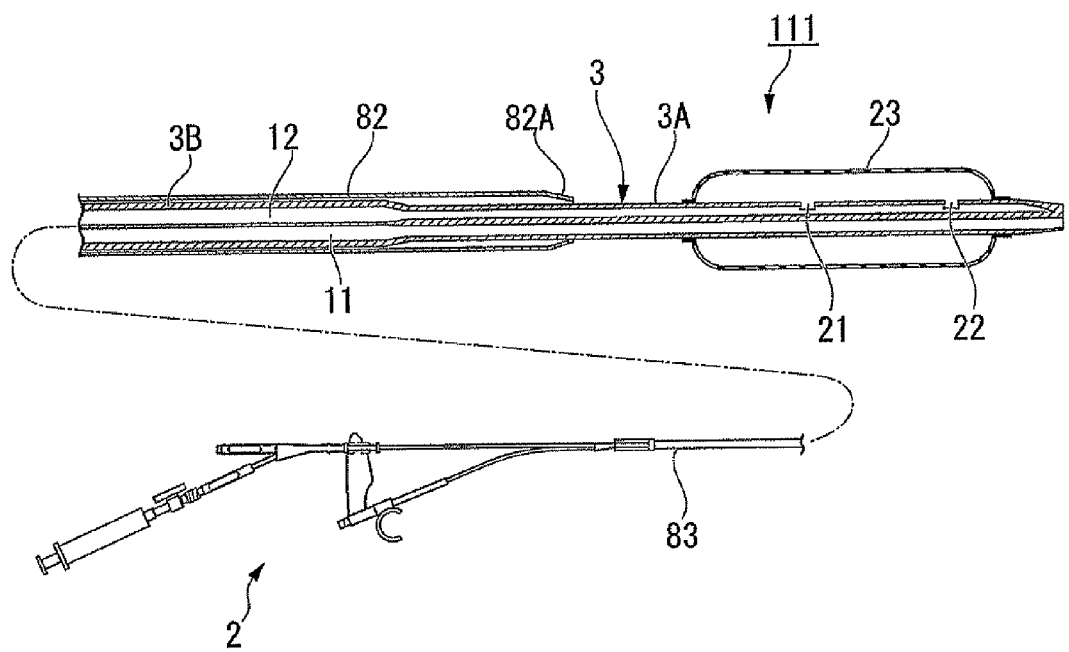
FIG. 43A is a diagram showing a state in which the whole balloon is swollen.
Figure 43B:
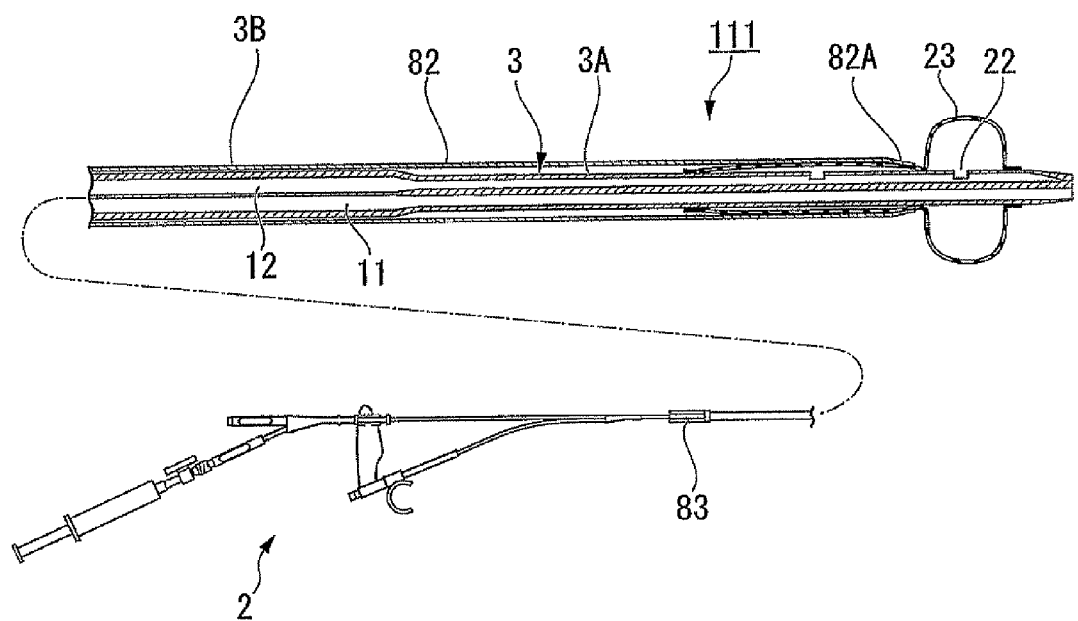
FIG. 43B is a diagram showing a state in which only a distal portion of the balloon is swollen.

The cover sheath 82 has a grip 83 which is attached to the proximal portion and a distal portion 82A which is reduced in diameter. An opening of the distal portion 82A is larger than the outer diameter of the shrunken balloon 23. When the balloon 23 is swollen, the balloon 23 is exposed from the cover sheath 82 to inject fluid, as shown in FIG. 43A. In addition, as shown in FIG. 43B, when the cover sheath 82 is disposed at a position corresponding to a substantial center in the axial direction of the balloon 23 and the fluid is then injected to the balloon 23, the balloon 23 is supplied with the fluid through the hole 22 or the one long hole as an alternative to the two holes 21 and 22, and only the exposed portion of the balloon 23 is swollen.

Next, a procedure using the medical instrument 111 will be described.

Figure 44:
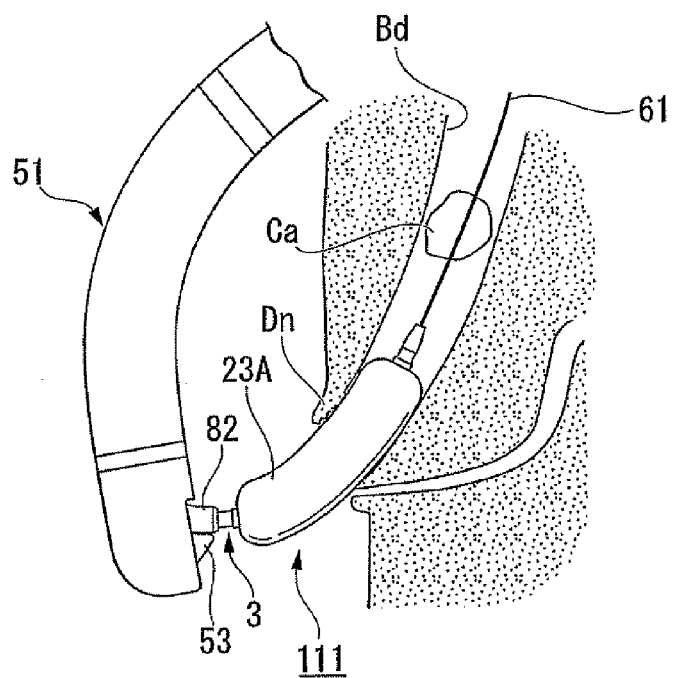
FIG. 44 is a diagram showing a state in which the balloon is swollen to press and enlarge a papilla.

After a papilla Dn is incised by a radio-frequency knife (not shown), the medical instrument 111 is introduced from the papilla Dn to a bile duct Bd along the guide wire 61. The cover sheath 82 is retreated in advance up to a position where the balloon 23 is completely exposed. The medical instrument 111 is advanced such that, for example, the substantial center of the balloon 23 reaches to the papilla Dn. As shown in FIG. 44, when the balloon 23 is swollen, the papilla Dn and the exit of the bile duct Bd are enlarged.

Figure 45:
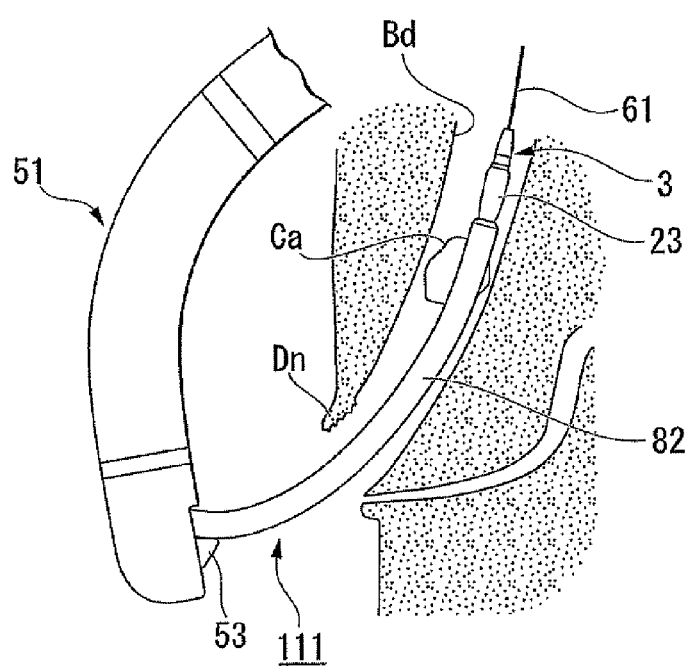
FIG. 45 is a diagram showing a state in which the medical instrument for an endoscope is advanced and the cover sheath is advanced such that substantially one half of the balloon is hidden.

After that, the fluid is drained from the balloon 23 to shrink the balloon. Since the fluid is drained through the two holes 21 and 22 or one end of the one long hole as an alternative of the two holes 21 and 22, the shrinkage can be securely performed even in the case where the balloon 23 is in close contact with the hole 21. Subsequently, the sheath 3 is fixed and the cover sheath 82 is advanced. Since the cover sheath 82 has the distal end which is reduced in diameter, the cover sheath can be easily inserted into the bile duct Bd. When substantially one half of the balloon 23 is covered with the cover sheath 82, the medical instrument 111 is further advanced into the back of the bile duct Bd. As shown in FIG. 45, the medical instrument 111 allows the exposed portion of the balloon 23 to be advanced deeper than a calculus Ca.

Figure 46:
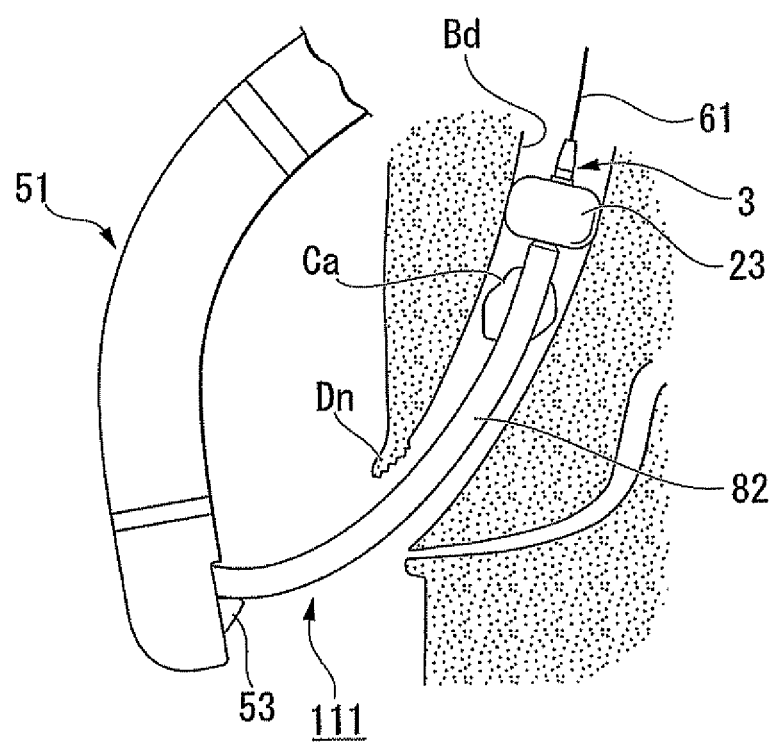
FIG. 46 is a diagram showing a state in which a distal side of the balloon is swollen.

As shown in FIG. 46, the balloon 23 is swollen. The balloon 23 is swollen such that the length in the axial direction is short and the bile duct Bd is blocked up. When the medical instrument 111 is retreated in the state in which the balloon 23 is swollen, the calculus Ca is discharged from the bile duct Bd so as to be scraped out by the balloon 23.

According to this embodiment, the same effect as that in the second embodiment is obtained.

Sixth Embodiment

Figure 47:
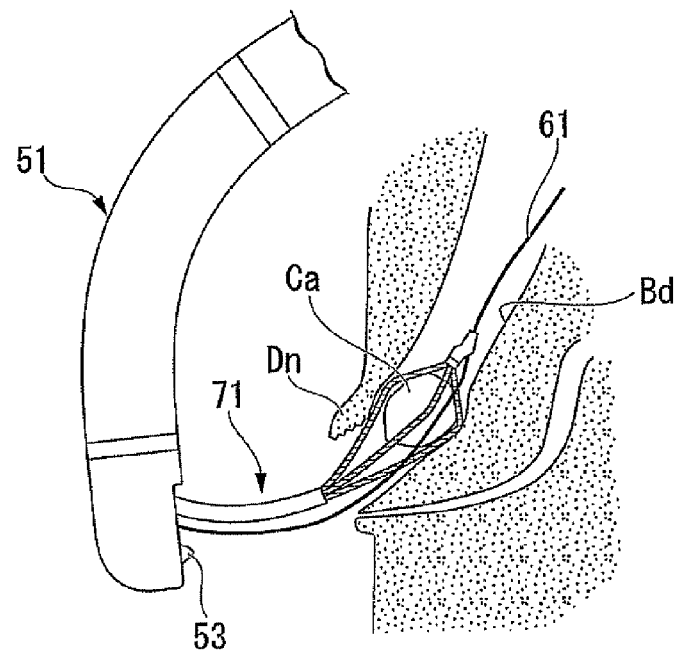
FIG. 47 is a diagram showing a state in which a calculus captured by a basket forceps is not extracted from a papilla.
Figure 48:
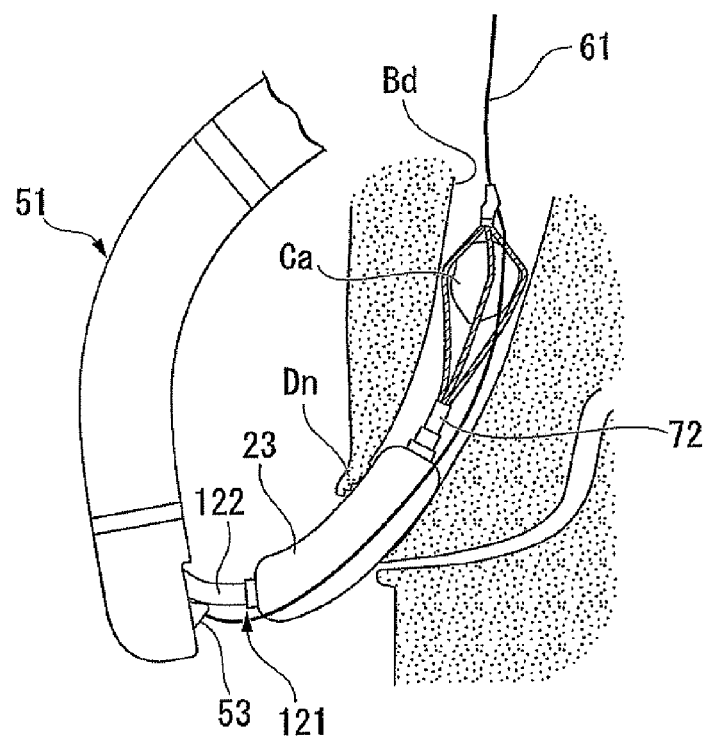
FIG. 48 is a diagram showing a state in which a medical instrument for an endoscope is allowed to pass as the basket forceps and the papilla is pressed and enlarged by a balloon.

This embodiment is realized when, as shown in FIG. 47, a calculus Ca is captured by a basket forceps 71 inserted after incision but cannot be removed from a papilla Dn because of the largeness of the calculus Ca. In this case, a medical instrument for an endoscope 121 (hereinafter, referred to as medical instrument) shown in FIG. 48 is used.

The medical instrument 121 has a flexible elongated sheath 122. The sheath 122 has a distal end which is reduced in diameter and a balloon 23 which is attached to an outer circumference of a distal side. In the sheath 122, a lumen into which a sheath 72 of the basket forceps 71 can be inserted and a lumen through which fluid to be supplied to the balloon 23 passes are formed. A proximal portion of the lumen (not shown) is provided with a mouth ring for supplying the fluid to the balloon 23 and is connected to a syringe (for example, syringe 106 in FIG. 40).

After a hand-side operating portion (not shown) of the basket forceps 71 is removed, the medical instrument 121 is introduced with the guide of the sheath 72 of the basket forceps 71 in a state in which the balloon 23 is shrunken. When substantially one half of the balloon 23 is inserted from the papilla Dn to an exit side of a bile duct, the fluid is supplied from the syringe. Since the balloon 23 is swollen, the papilla Dn and the exit side of the bile duct Bd are pressed and enlarged.

Figure 49:
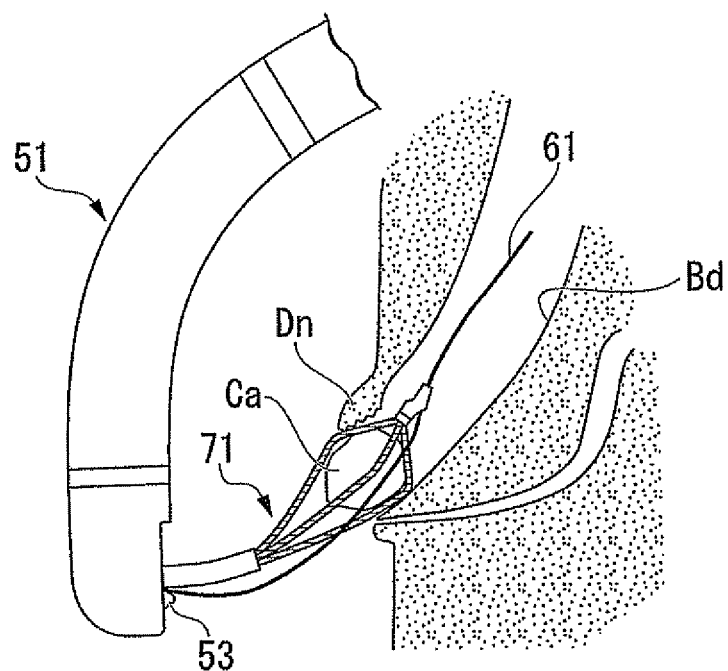
FIG. 49 is a diagram showing a state in which the calculus is discharged from the enlarged papilla.

After than, the balloon 23 is shrunken and the medical instrument 121 is then removed. Since the papilla Dn and the exit of the bile duct Bd are enlarged, the calculus Ca captured by the basket forceps 71 is extracted from the bile duct Bd, as shown in FIG. 49.

According to this embodiment, the medical instrument 121 with the balloon 23 is inserted to enlarge the opening of the channel, when the papilla Dn is incised to insert a medical instrument such as the basket forceps or the like but the calculus Ca cannot be discharged from the papilla Dn. Accordingly, a relatively large calculus Ca in the bile duct Bd also can be extracted without destruction. The procedure becomes simple and a burden of a patient is reduced.

Seventh Embodiment

This embodiment is realized when, as described in the sixth embodiment with reference to FIG. 47, a calculus Ca is captured by a basket forceps 71 inserted after incision but the basket forceps 71 cannot be removed from a papilla Dn because of the largeness of the calculus Ca.

Figure 50:
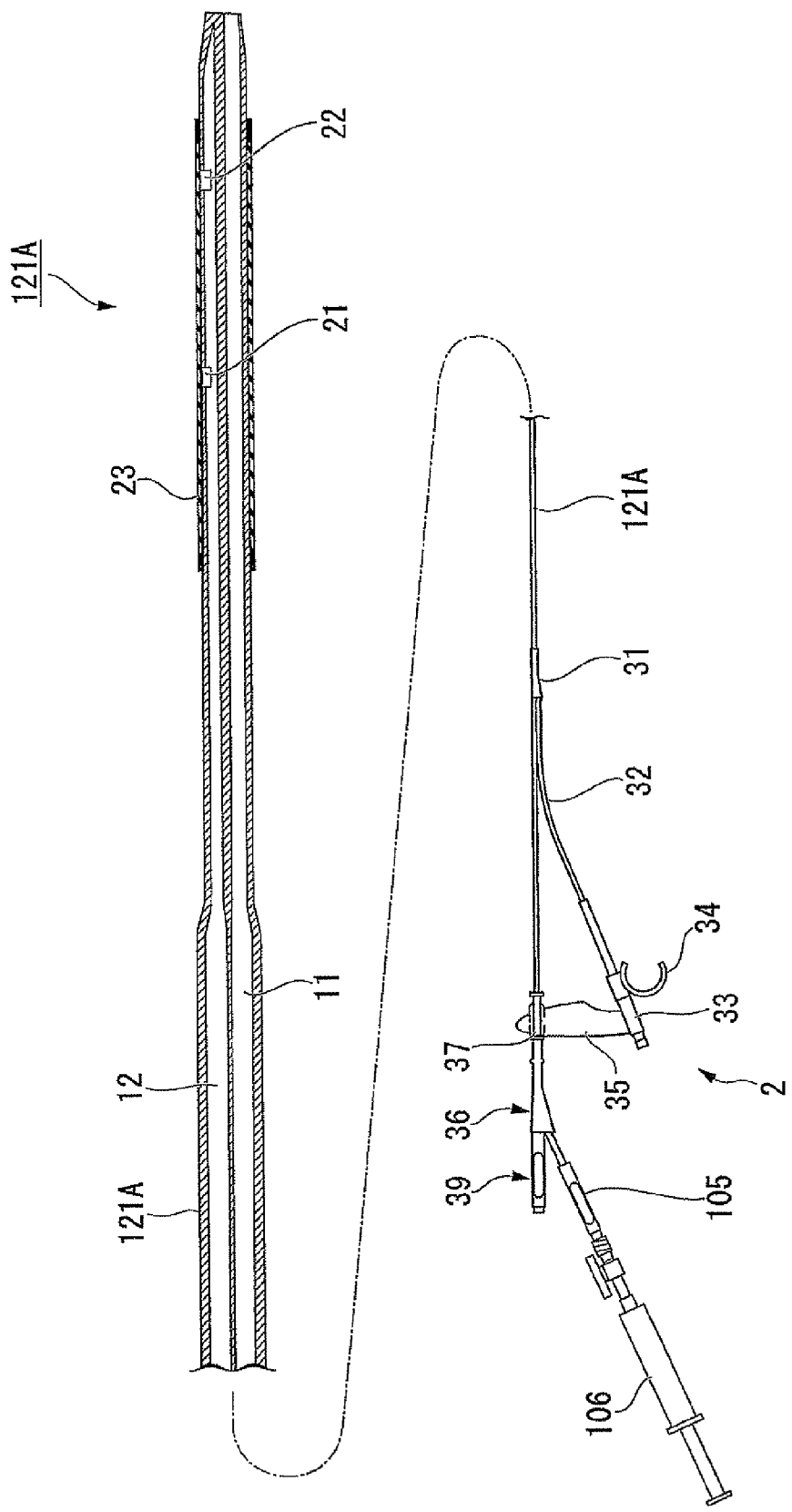
FIG. 50 is a diagram showing the configuration of a medical instrument for an endoscope having a catheter attached to a balloon.

FIG. 50 shows a medical instrument for an endoscope used in this procedure. The medical instrument for an endoscope 121A (hereinafter, referred to as medical instrument) has a flexible elongated sheath 122A and the sheath 122A has a balloon 23 attached to a distal portion thereof. The method of attaching the balloon 23, the material and the shape of the balloon 23, and the route for fluid supply are the same as in the above-described embodiment.

Figure 51:
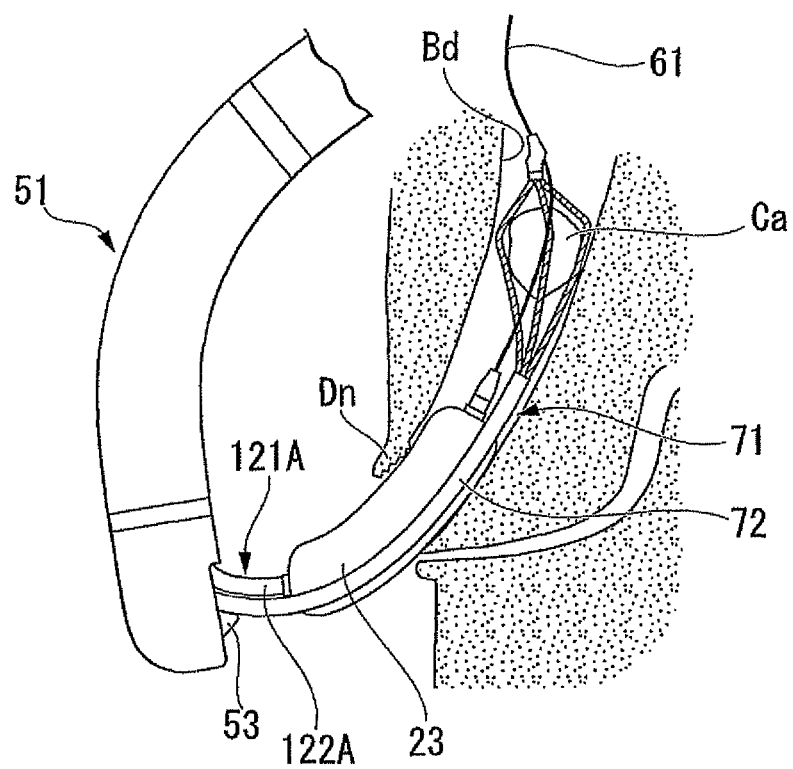
FIG. 51 is a diagram showing a state in which the medical instrument for an endoscope is inserted in parallel with a basket forceps and a papilla is pressed and enlarged by the balloon.

When the medical instrument 121A is used, a guide wire 61 is allowed to pass through a first lumen 11 of the sheath 122A and the medical instrument is introduced into a body along the guide wire 61. The medical instrument 121A is inserted substantially parallel to the basket forceps 71. The medical instrument 121A is inserted such that the substantial center of the balloon 23 reaches to the papilla Dn, and the balloon 23 is swollen by fluid from a syringe 106. As shown in FIG. 51, the balloon 23 is swollen and the papilla Dn and an exit side of a bile duct Bd are pressed and enlarged. Then, the balloon 23 is shrunken, and the medical instrument 121A is removed from the papilla Dn. Since the papilla Dn and the exit side of the bile duct Bd is enlarged, the calculus Ca captured by the basket forceps 71 is extracted from the bile duct Bd.

According to this embodiment, the same effect as that in the sixth embodiment is obtained. Since it is not necessary to pass the sheath 72 of the basket forceps 71 through the medical instrument 121A, an effort of removing the hand-side operating portion of the basket forceps 71 is saved and the sheath 122A of the medical instrument 121A can be reduced in diameter.

Eighth Embodiment

Figure 52:
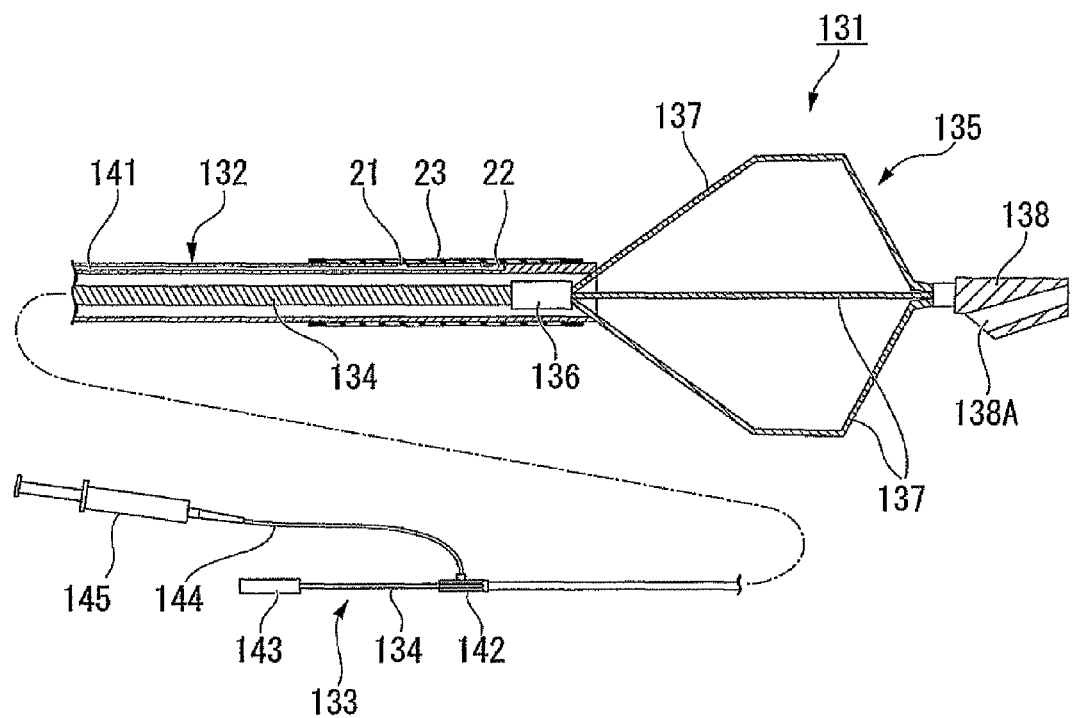
FIG. 52 is a diagram showing the configuration of a basket type forceps having a balloon.
Figure 53:
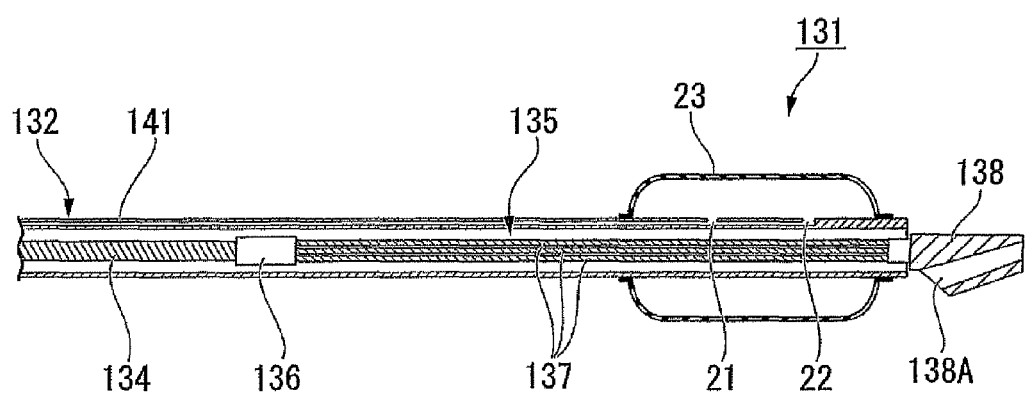
FIG. 53 is a diagram showing a state in which the balloon is swollen.

As shown in FIGS. 52 and 53, a basket forceps 131 which is a medical instrument for an endoscope has a flexible elongated sheath 132 and an operating portion 133 is provided in a proximal portion of the sheath 132. An operating wire 134 is allowed to pass through the sheath 132 so as to advance and retreat, and a distal end of the operating wire 134 has a basket-like treatment unit 135 attached thereto. The treatment unit 135 is configured such that one ends of a plurality of wires 137 are bound by a connecting member 136 fixed to the operating wire 134 and the other ends of the wires 137 are bound by a tip 138. The wires 137 are bound in the sheath 132 so as to be accommodated therein, however, the wires 137 are biased so as to open when projecting from the sheath 132. The tip 138 has a through hole 138A through which a guide wire passes and which is tilted relative to an axial line.

A balloon 23 is attached to an outer circumference of a distal portion of the sheath 132. A lumen 141 for supplying fluid to the balloon 23 is formed in the sheath 132. The lumen 141 communicates with the balloon 23 through two holes 21 and 22 or a long hole which is disposed instead of the two holes 21 and 22. The balloon 23 and the holes 21 and 22 are the same as in the above-described embodiment.

The operating portion 133 has a grip 142 fixed to the proximal portion of the sheath 132, and the operating wire 134 passes through the grip 142 to be drawn out. When an end portion 143 of the operating wire 134 is pushed with respect to the sheath 132, the treatment unit 135 at a distal end can project and retract from the sheath 132. Further, a tube 144 communicating with the lumen 141 extends from the grip 142 and a syringe 145 is attached to the tube 144.

The basket forceps 131 is configured, such that a papilla after incision is enlarged by the balloon 23 or a bile duct and the papilla are enlarged by the balloon 23 after a calculus Ca is captured by the treatment unit 135 in the bile duct Bd.

Ninth Embodiment

Figure 54:
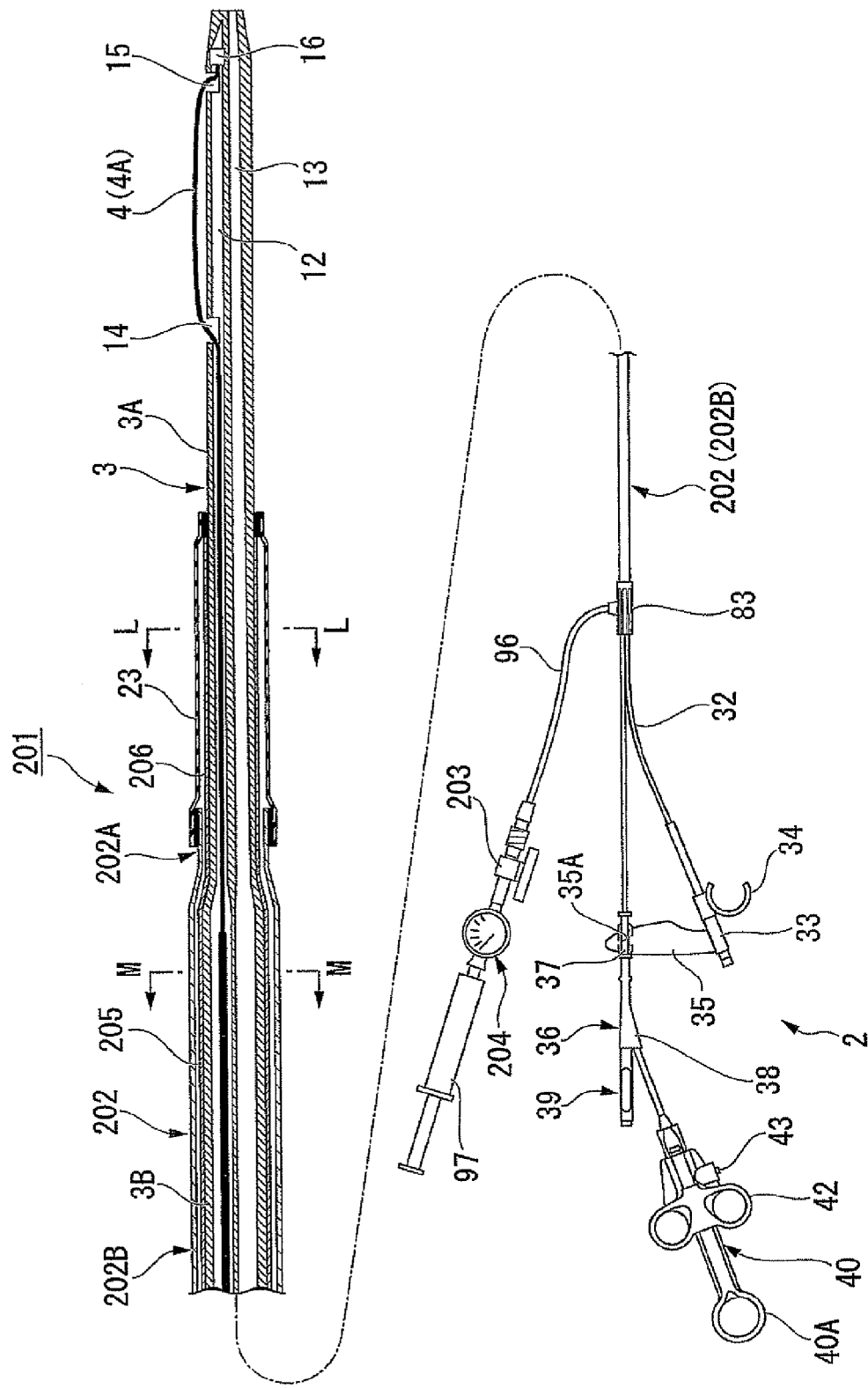
FIG. 54 is a diagram showing the configuration of a papillotome which is an example of a medical instrument for an endoscope.

FIG. 54 shows the configuration of a papillotome which is an example of a medical instrument for an endoscope. In the papillotome 201, the outside of a sheath 3 is covered with a cover sheath 202. Further, an end portion on a hand side of a balloon is connected to a distal end of the cover sheath 202 and a distal end of the balloon 23 is connected to an outer circumference of the sheath 3.

Figure 55:
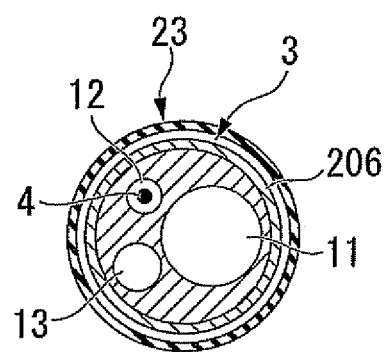
FIG. 55 is a cross-sectional view taken along the line L-L of FIG. 54.
Figure 56:
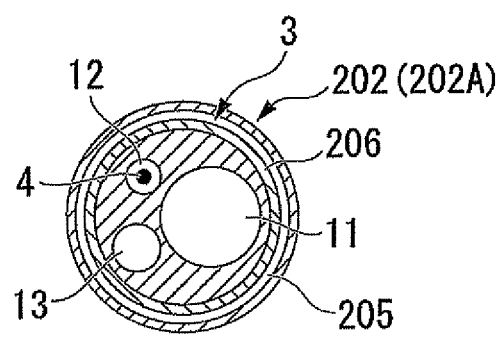
FIG. 56 is a cross-sectional view taken along the line M-M of FIG. 54.

As shown in FIGS. 55 and 56, in the sheath 3, three lumens 11, 12 and 13 are formed in parallel to each other in a longitudinal direction. The first lumen 11 has the largest diameter, is open at a distal end thereof, and is, for example, used to insert a guide wire thereto. The second lumen 12 has the smallest diameter and is sealed at a distal end thereof and has a conductive wire 4 passing therethrough. The third lumen 13 is open at a distal end thereof. A contrast agent is ejected from a distal end of the sheath 3 when a syringe is mounted on a mouth ring of a first operation unit 39 on a hand side.

The cover sheath 202 is elongated and flexible and has a balloon mounting portion 202A which is formed to mount the balloon 23 at a distal end. The balloon mounting portion 202A is thinner than the other portion 202B in accordance with the change in diameter of the sheath 3. On a hand side of the cover sheath 202, a grip 83 is mounted relative to the sheath 3 in an airtight manner. The grip 83 is connected to the syringe 97 through a tube 96, a stop cock 203, and a pressure gauge 204.

Figure 57:
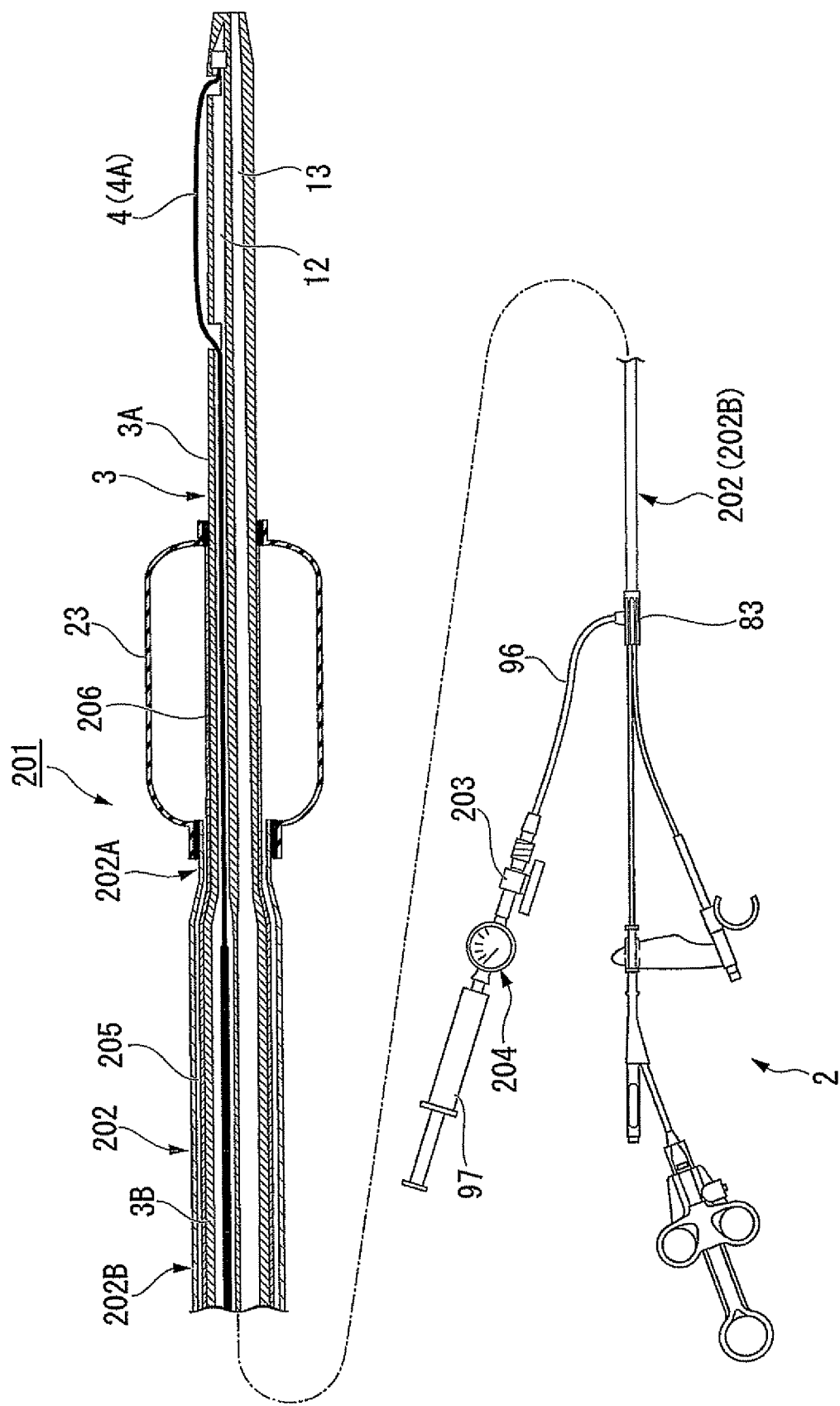
FIG. 57 is a diagram showing a state in which a balloon is swollen.

When fluid such as saline or air is supplied from the syringe 97 to the balloon 23 through an interval 205 between the sheath 3 and the cover sheath 202, the balloon 23 can be swollen, as shown in FIG. 57.

The shape, the size, and the material of the balloon 23 are the same as in the first and second embodiments.

A procedure using the papillotome 201 is the same as that in the first embodiment. However, since the interval 205 between the sheath 3 and the cover sheath 202 is used for a route for supplying the fluid to the balloon 23, it is convenient in that the lumen 13 can be used to inject the contrast agent therethrough. Further, thinning can be done by a portion which is not needed to provide a lumen for supplying fluid in the cover sheath 202 any more, and thus an outer diameter of the papillotome 201 can be reduced. Accordingly, insertion capability into a bile duct or an endoscope becomes better.

Further, the cover sheath 202 and the balloon 23 may be made of a non-elastomeric material and formed integrally with each other. In this case, since an effort of connecting the cover sheath 202 to the balloon 23 is saved, there is an advantage in that a manufacturing cost is reduced.

In addition, a rotation torque transmission member 206 may be disposed on the outer circumference of the sheath 3 in the interval 205. A distal end of the rotation torque transmission member 206 is fixed to the sheath 3 on the distal end of the balloon 23, or fixed to the sheath 3 with the balloon 23 by being matched with the distal end of the balloon 23. A rear end of the rotation torque transmission member 206 is fixed to the sheath and the grip 83 at a position of the grip 83. Accordingly, when the grip 83 is rotated in hand, a direction of an incision knife portion 4A can be adjusted to a desired direction.

A detailed specification of the rotation torque transmission member 206 includes, for example, a tube-like unit in which a plurality of bundles of thin stainless lines are knitted so as to be in a grid shape, a tube-like unit in which a stainless line or a stainless belt is wound in a coil shape of one or more number of turns, and a tube-like unit in which the coil of one or more number of turns is further wound in multilayers in an opposite direction.

Friction between the balloon 23 and a work channel 52 of an endoscope 51 is liable to be large. However, by extending the rotation torque transmission member 206 up to the distal side of the balloon 23, the rotation of the grip 83 in hand can be transmitted up to the distal side of the balloon 23, that is, up to the incision knife portion 4A. Further, an effort of assembling is saved by fixing the rotation torque transmission member 206 to the sheath 3 with the balloon 23. The cover sheath 202 and the balloon 23 also have roles of insulating and protecting the rotation torque transmission member 206 by positioning the rotation torque transmission member 206 in the interval 205. In addition, the outer diameter of the papillotome 201 also can be suppressed to a minimum.

Tenth Embodiment

Figure 58:
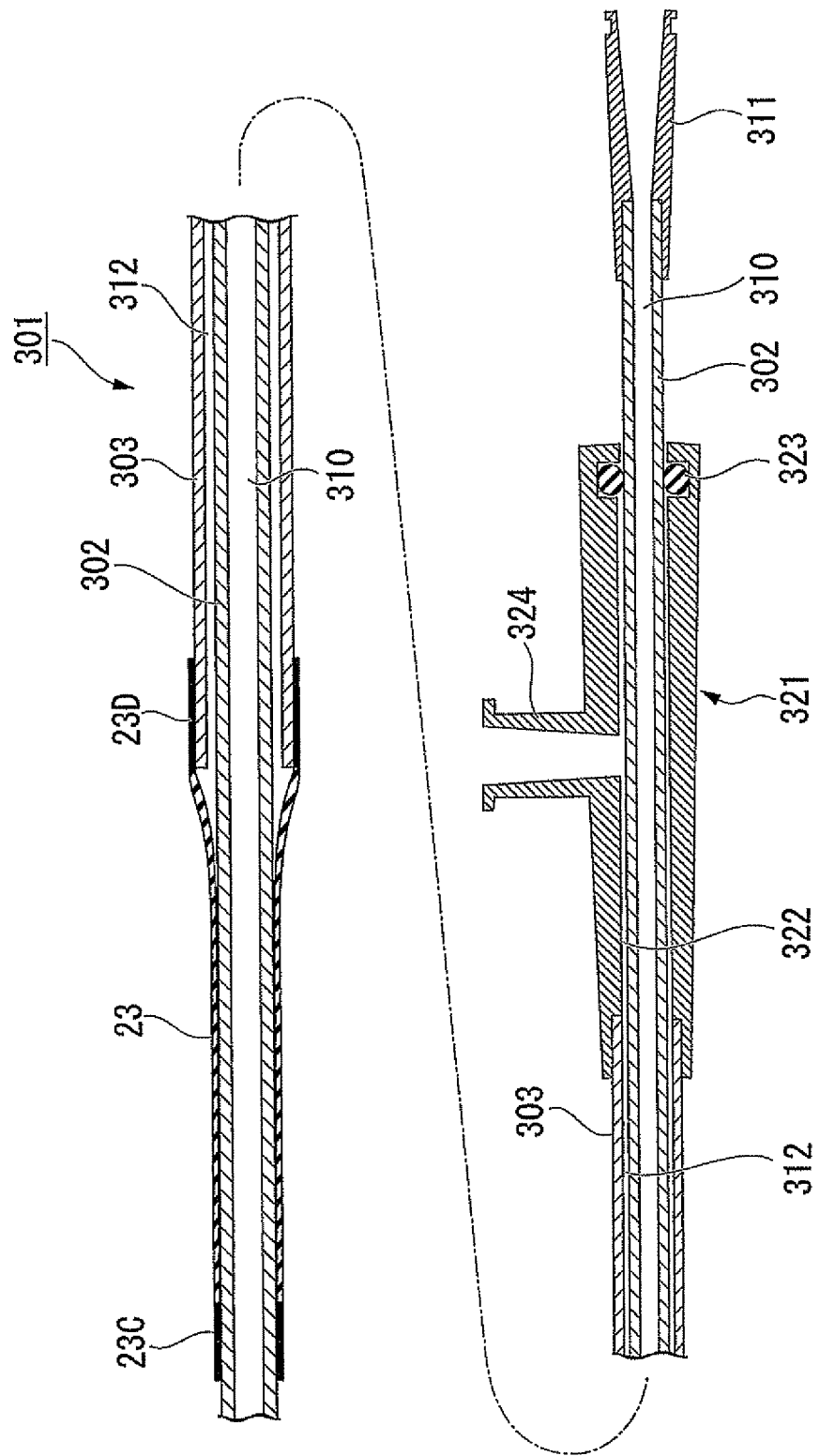
FIG. 58 is a diagram showing the configuration of a balloon catheter which is an example of a medical instrument for an endoscope.

FIG. 58 shows the configuration of a balloon catheter 301 which is an example of a medical instrument for an endoscope. The balloon catheter 301 is configured such that an outer sheath 303 covers the outside of a flexible elongated inner sheath 302 so as to advance and retreat. Further, an end portion on a hand side of a balloon 23 is connected to a distal end of the outer sheath 303, and the distal end of the balloon 23 is connected to an outer circumference of the inner sheath 302.

The inner sheath 302 has a lumen 310 which extends therethrough from a distal end to a proximal end, and a mouth ring 311 which is attached to a proximal portion and communicates with the lumen 310. From the mouth ring 311, a guide wire can be inserted and a contrast agent can be injected. A fixing end 23C on a distal side of the balloon 23 is fixed to an outer circumference of a distal portion of the inner sheath 302.

The shape and the size of the balloon 23 are the same as in the first and second embodiments. A fixing end 23D on a proximal side of the balloon 23 is fixed to an outer circumference of a distal portion of the outer sheath 303.

The outer sheath 303 has an inner diameter larger than an outer diameter of the inner sheath 302, and an interval 312 is formed therebetween. The interval 312 is used for a supply path for passing fluid for swelling the balloon 23 therethrough. A proximal end of the outer sheath 303 is fixed to an operating portion 321.

The operating portion 321 has through hole 322. The inner sheath 302 penetrates the through hole 322 so as to advance and retreat. Since a diameter of the through hole 322 is larger than the outer diameter of the inner sheath 302, the through hole 322 communicates with the interval 312. Seal members 323 are inserted on a proximal side of the operating portion 321 to make the inner sheath 302 slidable and form a water configuration or an airtight configuration. In addition, a mouth ring 324 communicating the through hole 322 protrudes the outside of a radial direction. The mouth ring 324 can be connected to a syringe for allowing the balloon 23 to be expanded and shrunken.

In FIG. 58, a position of the outer sheath 303 is set such that a distance between the fixing ends 23C and 23D of the balloon 23 is longer than an expansive diameter of the balloon 23. The position of the outer sheath 303 at this time is set as an initial position.

Next, a procedure using the balloon catheter 301 will be described.

Firstly, a papillotome (not shown) incises a papilla. In the state in which the guide wire is left in a bile duct, the papillotome is removed. Alternatively, the basket catheter 301 is introduced into a body along the guide wire to be inserted to the bile duct. At this time, the basket catheter 301 is inserted in a state in which the outer sheath 303 is disposed at the initial position, that is, in which the distance between the fixing ends 23C and 23D of the balloon 23 is larger than the largest expansive diameter of the balloon 23.

Figure 59:
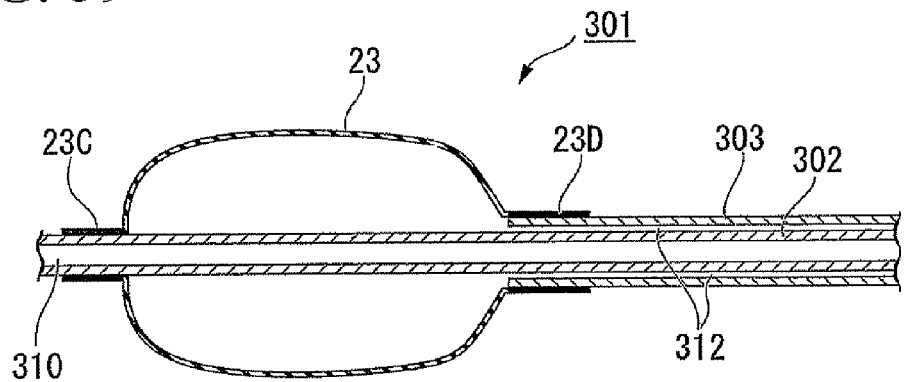
FIG. 59 is a cross-sectional view showing an enlarged distal portion when a balloon is swollen.

When a substantial center in an axial direction of the balloon 23 reaches to the papilla, fluid which is liquid or gas is injected from the syringe mounted on the mouth ring 324 of the operating portion 321 to the interval 312. The fluid is supplied from a distal end of the interval 312 to the balloon 23 to swell the balloon 23, as shown in FIG. 59. An expansive amount of the balloon 23 is adjusted by confirming an X-ray image or an endoscope image. When a pressure gauge is disposed between the syringe mounted on the mouth ring 324, the adjustment is performed by confirming a pressure indicated by the pressure gauge.

When the papilla and an exit side of the bile duct are pressed and enlarged by swelling the balloon 23, the fluid supplied to the balloon 23 is discharged. As shown in FIG. 58, the balloon 23 is swollen.

Figure 60:
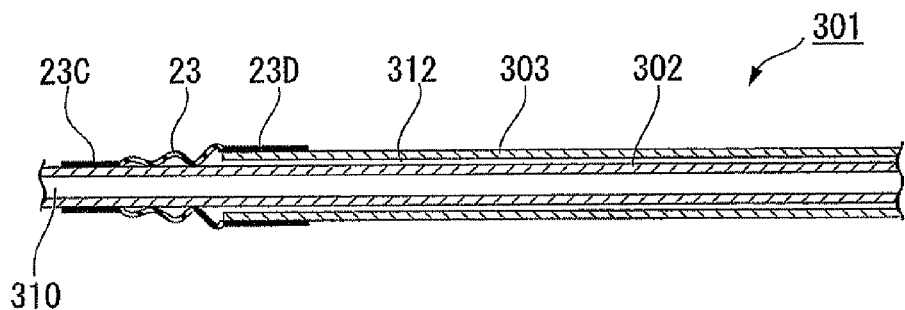
FIG. 60 is a diagram showing a state in which an outer sheath is relatively advanced in the state in which the balloon is shrunken.

Next, the operating portion 321 and the mouth ring 311 are gripped on the hand side and the inner sheath 302 retreats relative to the outer sheath 303. The outer sheath 303 advances relatively to the inner sheath 302. As shown in FIG. 60, the distance between the fixing ends 23C and 23D of the balloon 23 is reduced. The distance between the fixing ends 23C and 23D at this time is smaller than the largest expansive diameter of the balloon 23. In the state in which positions of both of the sheaths 302 and 303 relative to each other are fixed, the balloon catheter 301 is pushed until the fixing end 23D on a rear side of the balloon 23 advances in the rear of a calculus.

Figure 61:
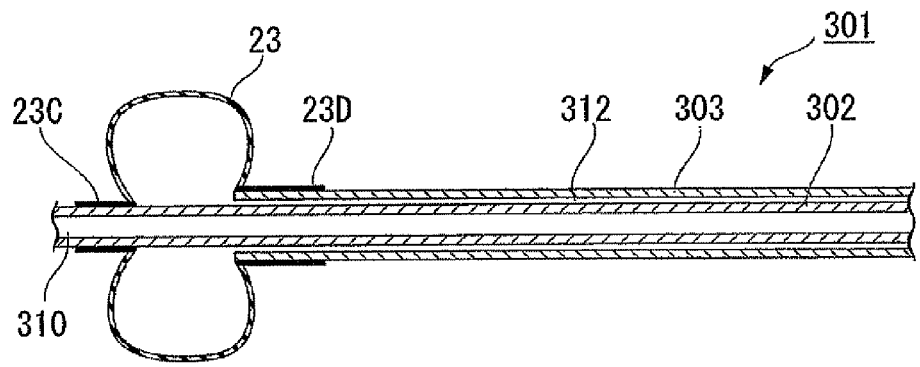
FIG. 61 is a diagram showing a state in which the balloon is swollen after the process of FIG. 60.

Fluid is supplied again from the syringe mounted on the mouth ring 324 to swell the balloon 23. As shown in FIG. 61, the balloon 23 is swollen such that a length thereof in the axial direction is larger than a length thereof in the radial direction. When the whole balloon catheter 301 is retreated in the state in which the balloon 23 is swollen, the calculus is caught by the balloon 23 and discharged from the bile duct so as to be scraped out. When the calculus is discharged, the balloon 23 is shrunken and the balloon catheter 301 is then removed from the endoscope. Here, when the largest expansive diameter of the balloon 23 is 20 mm, the distance between the fixing ends 23C and 23D of the balloon 23 can be changed from a distance larger than 20 mm to a distance smaller than 20 mm. Upon expansion, the length in the axial direction of the balloon 23 also extends. Accordingly, the length in the axial direction of the balloon 23 upon expansion is set so as to be larger than the distance between the fixing ends 23C and 23D. It is preferable that the distance between the fixing ends 23C and 23D is set to ½ or less of the largest expansive diameter of the balloon in order to reduce the length in the axial direction of the balloon 23 for complete contact with every corner of the bile duct and easy-of-use for collecting the calculus.

From the viewpoint that the balloon 23 is used for expanding the exit of the bile duct, it is necessary that the balloon 23 has a certain length in the axial direction so as to be prevented from sliding and from being displaced from the expanded portion of the channel. Accordingly, it is preferable that the distance between the fixing ends 23C and 23D is about 1.5 to 2 times the largest expansive diameter of the balloon.

When the strength of the expanded balloon 23 is treated as important, a non-elastomeric material, which has a small stretching property and a large strength, such as polyurethane, polyethylene, PET, or polyamide, is suitable for a material of the balloon 23. When an operating property, such as easiness of advancing and retreating in the bile duct, is treated as important, the balloon 23 may be made of an elastomeric material, which has a large stretching property, is shrunken upon shrinkage, and suppressed to a minimum in wrinkles upon reduction of the distance between the fixing ends 23C and 23D, such as latex, silicon rubber, urethane elastomer, or polyamide elastomer.

According to this embodiment, the swelling method of the balloon 23 is changed by the advancing and retreating operations of the outer sheath 303. When the distance between the fixing ends 23C and 23D are increased and the balloon 23 is then swollen, a large area of tissue can be pressurized, and a desired site of the channel can be securely expanded without displacement. However, when the distance between the fixing ends 23C and 23D are reduced and the balloon 23 is then expanded, the length in the axial direction is reduced, and thus displacement is easily performed along a curved shape of the duct. Accordingly, the calculus is easily discharged by the balloon 23.

In addition, in order to simplify the adjustment of the distance between the fixing ends 23C and 23D, marking for indicating the positions of both of the sheaths 302 and 303 relative to each other may be provided on the proximal side of the inner sheath 302 and the outer sheath 303, or a click may be provided for the operating portion 321. The inner sheath 302 may be used as a shape tube for a multi lumen, a basket, or a papillotome.

While preferred embodiments of the present invention have been described and illustrated above, it should be understood that these are exemplary of the present invention and are not to be considered as limiting. Additions, omissions, substitutions, and other modifications can be made without departing from the spirit or scope of the present invention. Accordingly, the present invention is not to be considered as being limited by the foregoing description, and is only limited by the scope of the appended claims.

What is claimed is:

1. A medical instrument for an endoscope to be used in the endoscope by being inserted therein, comprising:
   a flexible elongated sheath having a first lumen and a second lumen;
   a conductive wire which is inserted into the first lumen and of which a portion of a distal side is exposed to the outside of the sheath as a treatment unit; and
   a balloon which is attached to the sheath, is expandable with a supply of fluid from the second lumen, and is in close contact with the outer circumference of the sheath and an outer diameter of the balloon is equal to or less than an outer diameter of the sheath that is proximal to said balloon in an initial state of the balloon, and
   the outer diameter of the balloon is substantially constant in an axial direction,
   wherein the balloon is configured such that an axial dimension thereof is larger than a radial dimension upon expansion and a distal end of the balloon upon expansion is located closer to a proximal side of the sheath than the treatment unit exposed from the sheath.

2. A medical instrument for an endoscope according to claim 1, wherein the balloon is made of a non-elastomeric material and is folded and wound around an outer circumference of the sheath before expansion, and
   a proximal end of the treatment unit exposed from the sheath is disposed apart from the distal end of the balloon by 10 mm or more.

3. A treatment method using a medical instrument having a flexible elongate sheath, a conductive wire which is inserted into the sheath and of which a portion of a distal side is exposed to the outside of the sheath as a treatment unit, and a balloon which is attached to the sheath located closer to a proximal side of the sheath than the treatment unit and is configured such that an axial dimension thereof is larger than a radial dimension upon expansion, the method comprising the steps of:
   inserting the sheath into an instrument channel of an endoscope to be introduced into a body cavity;
   applying electric current to the treatment unit to incise a tissue in the body cavity and enlarge a diameter of a body channel;
   inserting the sheath into the body channel and moving the balloon up to a position of the incised tissue;
   expanding the balloon for a first time to further enlarge the diameter of the body channel at the position of the tissue
   after expanding the balloon for the first time, shrinking the balloon and then advancing the sheath further into the body channel to move the balloon to a position deeper than a calculus in the body channel;
   expanding the balloon for a second time such that an axial dimension thereof is smaller than that in the step of expanding the balloon for the first time; and
   removing the sheath from the body channel in the state in which the balloon is expanded to discharge the calculus from the body channel.

4. A treatment method using a medical instrument having a flexible elongate sheath, a conductive wire which is inserted into the sheath and of which a portion of a distal side is exposed to the outside of the sheath as an instrument unit, and a balloon which is attached to the sheath located closer to a proximal side of the sheath than the instrument unit, is configured such that an axial dimension thereof is larger than a radial dimension upon expansion, and is in close contact with the outer circumference of the sheath, and an outer diameter of the balloon is equal to or less than an outer diameter of the portion of the sheath that is proximal to said balloon in an initial state of the balloon, and
   the outer diameter of the balloon is substantially constant in an axial direction,
   the method comprising the steps of:
   inserting the sheath into an instrumental channel of an endoscope to be introduced into a body cavity;
   applying electric current to the treatment unit to incise a tissue in the body cavity and enlarge a diameter of a body channel;
   inserting the sheath into the body channel and moving the balloon up to a position of the incised tissue; and
   expanding the balloon to further enlarge the diameter of the body channel at the position of the tissue.

* * * * *